US010183085B2

(12) United States Patent
Dobrinsky et al.

(10) Patent No.: US 10,183,085 B2
(45) Date of Patent: Jan. 22, 2019

(54) ULTRAVIOLET-BASED DETECTION AND STERILIZATION

(71) Applicant: Sensor Electronic Technology, Inc., Columbia, SC (US)

(72) Inventors: Alexander Dobrinsky, Loudonville, NY (US); Michael Shur, Latham, NY (US); Remigijus Gaska, Columbia, SC (US); Timothy James Bettles, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 15/436,945

(22) Filed: Feb. 20, 2017

(65) Prior Publication Data
US 2017/0157276 A1    Jun. 8, 2017

Related U.S. Application Data

(63) Continuation of application No. 14/883,804, filed on Oct. 15, 2015, now Pat. No. 9,572,903.
(Continued)

(51) Int. Cl.
*G01J 1/42* (2006.01)
*A61L 2/10* (2006.01)
(Continued)

(52) U.S. Cl.
CPC ............. *A61L 2/10* (2013.01); *A41D 13/002* (2013.01); *A61L 2/24* (2013.01); *A61L 9/00* (2013.01);
(Continued)

(58) Field of Classification Search
CPC ..... A61L 2/10; A61L 2/24; A61L 9/20; A41D 13/002; G01J 1/429; G01N 21/6456; G09B 5/06; G09B 19/24
See application file for complete search history.

(56) References Cited

U.S. PATENT DOCUMENTS 5,024,594 A    6/1991  Athayde et al.
5,359,735 A   11/1994  Stockwell
(Continued)

FOREIGN PATENT DOCUMENTS

EP    2400866 B1    5/2013

OTHER PUBLICATIONS

Vu, M., Application No. 14883804, Notice of Allowance, dated Oct. 13, 2016, 17 pages.
(Continued)

*Primary Examiner* — Kiho Kim
(74) *Attorney, Agent, or Firm* — LaBatt, LLC

(57) ABSTRACT

A system capable of detecting and/or sterilizing surface(s) of an object using ultraviolet radiation is provided. The system can include a disinfection chamber and/or handheld ultraviolet unit, which includes ultraviolet sources for inducing fluorescence in a contaminant and/or sterilizing a surface of an object. The object can comprise a protective suit, which is worn by a user and also can include ultraviolet sources for disinfecting air prior to the air entering the protective suit. The system can be implemented as a multi-tiered system for protecting the user and others from exposure to the contaminant and sterilizing the protective suit after exposure to an environment including the contaminant.

20 Claims, 18 Drawing Sheets

Related U.S. Application Data

(60) Provisional application No. 62/064,101, filed on Oct. 15, 2014, provisional application No. 62/065,180, filed on Oct. 17, 2014, provisional application No. 62/066,459, filed on Oct. 21, 2014, provisional application No. 62/069,490, filed on Oct. 28, 2014, provisional application No. 62/076,256, filed on Nov. 6, 2014.

(51) Int. Cl.
| | |
|---|---|
| *A61L 2/24* | (2006.01) |
| *A61L 9/20* | (2006.01) |
| *G01N 21/64* | (2006.01) |
| *A61L 9/00* | (2006.01) |
| *A41D 13/002* | (2006.01) |
| *G09B 5/06* | (2006.01) |
| *G09B 19/24* | (2006.01) |

(52) U.S. Cl.
CPC ............ *A61L 9/20* (2013.01); *G01J 1/429* (2013.01); *G01N 21/6456* (2013.01); *G01N 21/6486* (2013.01); *G09B 5/06* (2013.01); *G09B 19/24* (2013.01); *A61L 2202/14* (2013.01); *A61L 2209/111* (2013.01); *A61L 2209/14* (2013.01); *G01N 2201/0221* (2013.01)

(56) References Cited

U.S. PATENT DOCUMENTS

| | | | |
|---|---|---|---|
| 7,553,456 | B2 | 6/2009 | Gaska et al. |
| 7,634,996 | B2 | 12/2009 | Gaska et al. |
| 8,032,952 | B2 | 10/2011 | Plut |
| 8,277,724 | B2 | 10/2012 | Jung et al. |
| 8,277,734 | B2 | 10/2012 | Koudymov et al. |
| 8,378,324 | B2 | 2/2013 | Gardner, III |
| 8,771,330 | B1 | 7/2014 | Roper et al. |
| 8,980,178 | B2 | 3/2015 | Gaska et al. |
| 9,006,680 | B2 | 4/2015 | Bettles et al. |
| 9,138,499 | B2 | 9/2015 | Bettles et al. |
| 2002/0187066 | A1* | 12/2002 | Yu ............... A61L 2/0011 422/22 |
| 2005/0045178 | A1* | 3/2005 | Tang ............ A41D 13/0025 128/202.19 |
| 2005/0193945 | A1* | 9/2005 | Coffield ........... A61M 35/00 118/704 |
| 2007/0231189 | A1 | 10/2007 | Jung et al. |
| 2009/0280035 | A1 | 11/2009 | Koudymov et al. |
| 2010/0175694 | A1 | 7/2010 | James et al. |
| 2010/0296971 | A1 | 11/2010 | Gaska et al. |
| 2012/0223216 | A1 | 9/2012 | Flaherty et al. |
| 2012/0311926 | A1 | 12/2012 | Mittelmark et al. |
| 2013/0048545 | A1 | 2/2013 | Shatalov et al. |
| 2013/0270445 | A1 | 10/2013 | Gaska et al. |
| 2013/0281956 | A1 | 10/2013 | Mulcahey et al. |
| 2014/0060094 | A1 | 3/2014 | Shur et al. |
| 2014/0060095 | A1 | 3/2014 | Shur et al. |
| 2014/0060096 | A1 | 3/2014 | Shur et al. |
| 2014/0060104 | A1 | 3/2014 | Shur et al. |
| 2014/0061509 | A1 | 3/2014 | Shur et al. |
| 2014/0079587 | A1 | 3/2014 | Dayton |
| 2014/0183377 | A1 | 7/2014 | Bettles et al. |
| 2014/0202962 | A1 | 7/2014 | Bilenko et al. |
| 2014/0264070 | A1 | 9/2014 | Bettles et al. |
| 2014/0264076 | A1 | 9/2014 | Bettles et al. |
| 2014/0341777 | A1* | 11/2014 | Deshays ............ A61L 2/24 422/24 |
| 2014/0346370 | A1 | 11/2014 | Dobrinsky et al. |
| 2015/0008167 | A1 | 1/2015 | Shturm et al. |
| 2015/0069270 | A1 | 3/2015 | Shur et al. |
| 2015/0165079 | A1 | 6/2015 | Shur et al. |
| 2015/0217011 | A1 | 8/2015 | Bettles et al. |
| 2015/0297767 | A1 | 10/2015 | Gaska et al. |
| 2015/0336810 | A1 | 11/2015 | Smetona et al. |
| 2016/0000953 | A1 | 1/2016 | Bettles et al. |
| 2016/0058020 | A1 | 3/2016 | Shur et al. |
| 2016/0074547 | A1 | 3/2016 | Dobrinsky et al. |
| 2016/0077278 | A1 | 3/2016 | Dobrinsky et al. |
| 2016/0077292 | A1 | 3/2016 | Dobrinsky et al. |
| 2016/0088868 | A1 | 3/2016 | Dobrinsky et al. |
| 2016/0106873 | A1 | 4/2016 | Dobrinsky et al. |
| 2016/0114067 | A1 | 4/2016 | Dobrinsky et al. |
| 2016/0114186 | A1 | 4/2016 | Dobrinsky et al. |
| 2016/0128526 | A1 | 5/2016 | Dobrinsky et al. |
| 2016/0324996 | A1 | 11/2016 | Bilenko et al. |
| 2017/0057842 | A1 | 3/2017 | Dobrinsky et al. |
| 2017/0100494 | A1 | 4/2017 | Dobrinsky et al. |
| 2017/0100495 | A1 | 4/2017 | Shur et al. |
| 2017/0100496 | A1 | 4/2017 | Shur et al. |
| 2017/0189711 | A1 | 7/2017 | Shur et al. |

OTHER PUBLICATIONS

Han, I., International Application No. PCT/US2015/055646, International Serach Report and Written Opinion, dated Feb. 5, 2016, 11 pages.

Kim, K., U.S. Appl. No. 15/835,068, Office Action 1, dated Oct. 1, 2018, 16 pages.

* cited by examiner

FIG. 1
*Prior Art*

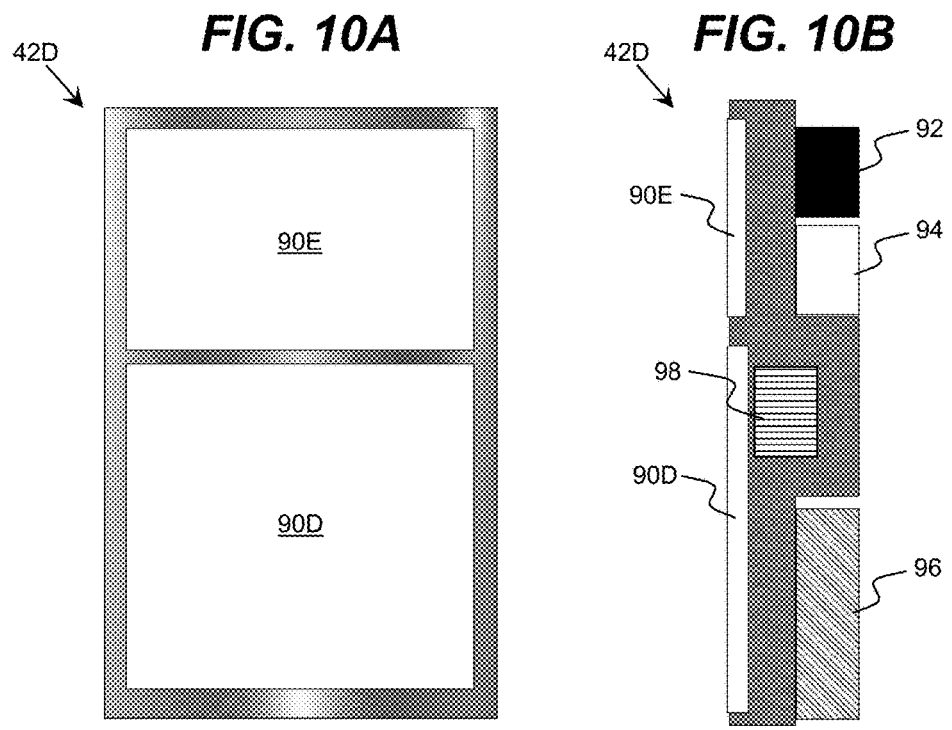

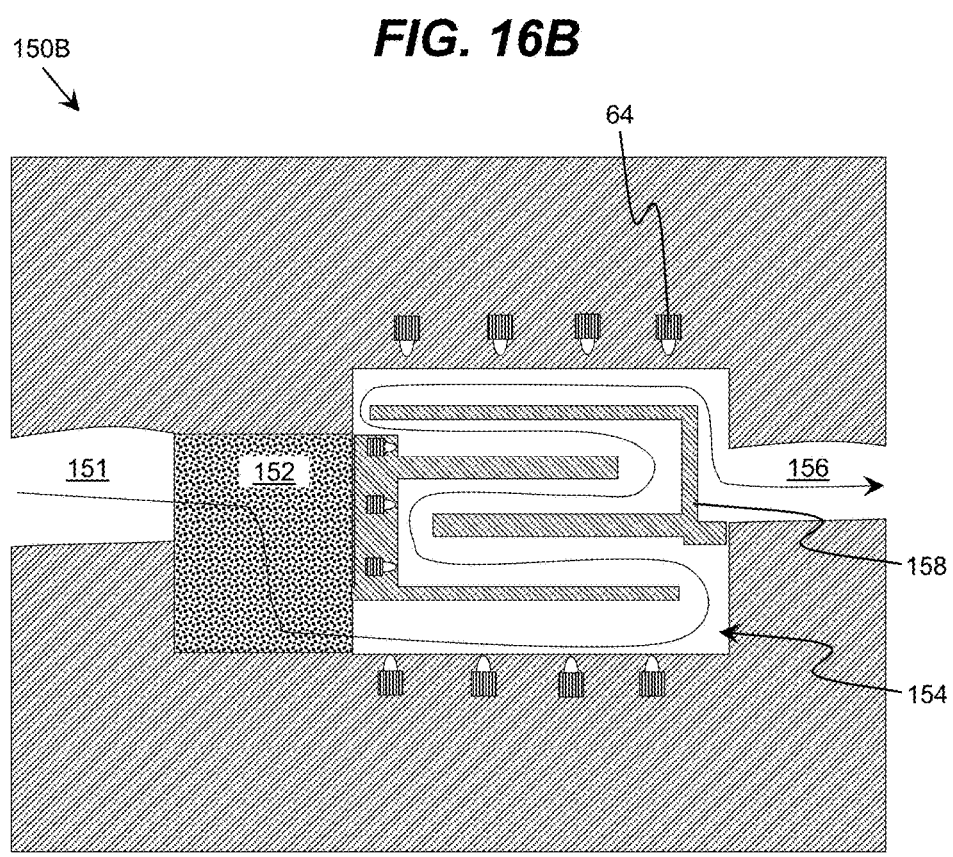

ULTRAVIOLET-BASED DETECTION AND STERILIZATION

REFERENCE TO RELATED APPLICATIONS

The current application is a continuation of U.S. patent application Ser. No. 14/883,804, filed on 15 Oct. 2015, which claims the benefit of: U.S. Provisional Application No. 62/064,101, which was filed on 15 Oct. 2014; U.S. Provisional Application No. 62/065,180, which was filed on 17 Oct. 2014; U.S. Provisional Application No. 62/076,256, which was filed on 6 Nov. 2014; U.S. Provisional Application No. 62/066,459, which was filed on 21 Oct. 2014, and U.S. Provisional Application No. 62/069,490, which was filed on 28 Oct. 2014, each of which is hereby incorporated by reference.

TECHNICAL FIELD

The disclosure relates generally to surface and air sterilization, and more particularly, to an ultraviolet-based solution for sterilizing surfaces and air using ultraviolet radiation.

BACKGROUND ART

Chemical-biological protective suits are worn when the surrounding environment may present a potential hazard of exposing an individual to potentially harmful or fatal chemical or biological agents. Exposure to such agents may be the result of accidental release in a scientific or medical laboratory, or in a hospital; intentional release by a government to attack the military forces of the opposition; and/or release during peacetime by criminal or terrorist organizations with the purpose of creating mayhem, fear and widespread destruction. The protective suits further can be useful for protecting personnel treating others during a viral or biological epidemic. For these reasons, the development of reliable, adequate protection against biological and chemical agents is desirable.

Historically, the materials used for chemical-biological protective suits are unbreathable. As a result, the use of these materials retards the ability of the human body to dissipate heat through perspiration, resulting in the development of heat stress burden on the wearer. For example, currently commercially available materials generally produce a heat stress burden on the person wearing the suit.

Furthermore, current commercially available chemical and biological protective suits also lack a mechanism to detoxify chemical and biological agents. These types of suits possess adsorptive chemical protective systems that act by adsorbing hazardous liquids and vapors into adsorbents thus passively inhibiting the hazardous materials from reaching the individual wearing the suit. However, these adsorbents are limited by a finite ability to adsorb chemicals. Furthermore, adsorbents indiscriminately adsorb chemical species for which protection is unnecessary, thereby reducing the available capacity for adsorption of the chemicals to which they were intended to provide protection.

The anti-microbial properties of UV-C light (Ultraviolet light-C band) are well-known to scientists and have been used since the 1930's to kill germs containing DNA and RNA (including bacteria, viruses, fungi and mold). UV-C light is invisible to the human eye. While UV-C light is invisible, given sufficient intensity and exposure, UV-C light can kill most of the germs responsible for causing disease in humans and animals. UV-C light can destroy the DNA and/or RNA (genetic material) of pathogens (disease-causing bacteria, viruses, mold, etc.). Once the DNA in a pathogen has been destroyed, the pathogen is either killed or deactivated; the pathogen can no longer function properly; and the pathogen can no longer reproduce.

In general, ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, ultraviolet light, and in particular, UV-C light is "germicidal," i.e., it deactivates the DNA of bacteria, viruses and other pathogens and thus destroys their ability to multiply and cause disease. This effectively results in sterilization of the microorganisms. Specifically, UV-C light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 280 nm provides the highest germicidal effectiveness. While susceptibility to UV light varies, exposure to UV energy for about 20 to about 34 milliwatt-seconds/cm$^2$ is adequate to deactivate approximately 99 percent of the pathogens.

Various approaches have sought to use ultraviolet light to disinfect a compartment, such as compartments found in refrigerators. For example, one approach proposes a plurality of small, low current UV lights which utilize the standard circuitry of the refrigerator to power the UV light source. Another approach uses a UV lamp installed in a top portion of the refrigerator and reflective lining throughout the interior to reflect the UV radiation throughout the compartment. Another approach provides a UV system with a single UV source attached to an internal sidewall of a refrigerator to radiate light to the entire compartment, or in the alternative, provide UV exposure to a limited compartment. Still another approach proposes an air cleaner for an internal compartment of a refrigerator, which utilizes a UV filter to reduce pathogens in the re-circulated air. Still another approach provides a refrigerator with UV light irradiation components to eradicate low-level light from the storage containers contained therein to promote freshness of foodstuffs.

Box-type UV sterilizers are well known for use in sterilizing all manner of objects, including contact lenses, combs and safety goggles. Often only a single source of radiation is employed in these sterilizers and, as such, there are often areas on an object to be sterilized that are shadowed from the UV radiation produced from the single source. Furthermore, the object to be sterilized is often required to rest on a support during the sterilization process. When the support is not transparent to the UV radiation, the support also contributes to shadowing the object to be sterilized from the UV radiation.

Various approaches have been used in decontaminating surfaces through the use of ultraviolet light. One approach includes a mobile germicidal system for decontaminating walls and a ceiling of a room, in which germicidal lamps are positioned adjacent the wall and/or ceiling to thereby sterilize the surface. Another approach proposes an ultraviolet air sterilization device for connection to an air handling duct for the purpose of sterilizing the air as it flows through the duct. Still another approach describes a wheeled carriage with a handle to allow the operator to move the sterilization device over a floor. Other approaches seek to provide a handheld device for moving across a surface to eradicate undesirable elements thereon, a mobile disinfectant device and method using ultraviolet light to sterilize a surface; and a UV spot curing system for hardening epoxy material using a wand emitting ultraviolet light.

SUMMARY OF THE INVENTION

In light of the above, the inventors recognize a need for a breathable protective suit, which provides robust protection for an individual wearing the suit. The inventors further propose a system including a chamber within which the suit can be sterilized against microorganisms, such as viruses and bacteria, and/or a handheld ultraviolet unit, which can be used to detect microorganisms on a surface of the suit and/or sterilize the surface. While aspects of the invention are described in conjunction with a protective suit, it is understood that embodiments can be directed to the evaluation and/or sterilization of any of various types of objects.

Aspects of the invention provide a system capable of detecting and/or sterilizing surface(s) of an object using ultraviolet radiation. The system can include a disinfection chamber and/or handheld ultraviolet unit, which includes ultraviolet sources for inducing fluorescence in a contaminant and/or sterilizing a surface of an object. The object can comprise a protective suit, which is worn by a user and also can include ultraviolet sources for disinfecting air prior to the air entering the protective suit. The system can be implemented as a multi-tiered system for protecting the user and others from exposure to the contaminant and sterilizing the protective suit after exposure to an environment including the contaminant.

A first aspect of the invention provides a system comprising: a disinfection chamber comprising: a set of ultraviolet disinfection sources configured to irradiate an object located within the disinfection chamber from a plurality of directions; a set of ultraviolet fluorescent sources configured to irradiate at least a portion of the object with ultraviolet radiation configured to induce fluorescence in a target contaminant; and a set of cameras configured to acquire image data of the object from a plurality of directions; and a computer system including a set of computing devices, wherein the computer system is configured to perform a sterilization procedure for the object, wherein the sterilization procedure includes processing the image data to evaluate shadow data and fluorescence data to adjust sterilization of the object using the set of ultraviolet sources.

A second aspect of the invention provides a system comprising: a protective suit worn by a user, wherein the protective suit completely isolates the user from exposure to contaminants in an environment; and a disinfection chamber for sterilizing an exterior surface of the protective suit, the disinfection chamber comprising: a set of ultraviolet disinfection sources configured to irradiate the protective suit from a plurality of directions; a set of ultraviolet fluorescent sources configured to irradiate at least a portion of the protective suit with ultraviolet radiation configured to induce fluorescence in a target contaminant; and a set of cameras configured to acquire image data of the protective suit from a plurality of directions; and a computer system including a set of computing devices, wherein the computer system is configured to perform a sterilization procedure for the protective suit, wherein the sterilization procedure includes processing the image data to evaluate shadow data and fluorescence data to adjust sterilization of the protective suit using the set of ultraviolet sources.

A third aspect of the invention provides a system including: a handheld ultraviolet unit configured to induce fluorescence in a target contaminant on an adjacent surface, detect the fluorescence on the adjacent surface, and provide location data regarding a location of the fluorescence for processing by an external computer system; a disinfection chamber comprising: a set of ultraviolet disinfection sources configured to irradiate an object located within the disinfection chamber from a plurality of directions; and a set of cameras configured to acquire image data of the object from a plurality of directions; and a computer system including a set of computing devices, wherein the computer system is configured to perform a sterilization procedure for the object, wherein the sterilization procedure includes adjusting operation of the set of ultraviolet disinfection sources based on the location data and the image data.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 1 shows a log reduction of the Ebola virus as a function of radiative dose according to the prior art.

FIG. 2 shows a high level diagram of an illustrative protection system according to an embodiment.

FIG. 3 shows a more detailed view of an illustrative protection system according to an embodiment.

FIG. 4 shows a component-level view of an illustrative protection system according to an embodiment.

FIG. 5 shows an illustrative decontamination chamber according to an embodiment.

FIGS. 6A and 6B show another illustrative decontamination chamber according to an embodiment.

FIG. 7 shows still another illustrative decontamination chamber according to an embodiment.

FIG. 8 shows an illustrative handheld ultraviolet unit according to an embodiment.

FIGS. 9A and 9B show illustrative handheld ultraviolet units according to embodiments.

FIGS. 10A and 10B show front and side views, respectively, of an illustrative handheld ultraviolet unit according to another embodiment.

FIG. 11A shows a side view of an illustrative handheld ultraviolet unit according to still another embodiment, and FIG. 11B illustrates illumination of a surface by the handheld ultraviolet unit.

FIG. 12 shows an illustrative process for sterilizing a surface according to an embodiment.

FIG. 13 shows an illustrative protective suit according to an embodiment.

FIG. 14 shows an illustrative embodiment for facilitating effective sterilization of a protective suit according to an embodiment.

FIG. 15 shows an illustrative mask according to an embodiment.

FIGS. 16A-16C show illustrative ultraviolet disinfection chambers according to embodiments.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 2:
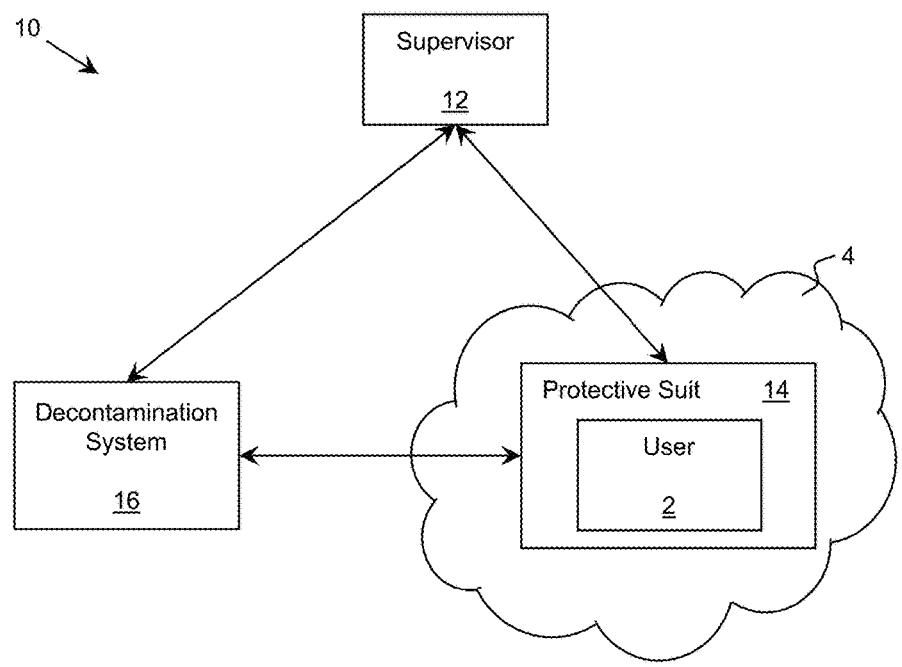

As indicated above, aspects of the invention provide a system capable of detecting and/or sterilizing surface(s) of an object using ultraviolet radiation. The system can include a disinfection chamber and/or handheld ultraviolet unit, which includes ultraviolet sources for inducing fluorescence in a contaminant and/or sterilizing a surface of an object. The object can comprise a protective suit, which is worn by a user and also can include ultraviolet sources for disinfecting air prior to the air entering the protective suit. The system can be implemented as a multi-tiered system for protecting the user and others from exposure to the contaminant and sterilizing the protective suit after exposure to an environment including the contaminant.

It is understood that, unless otherwise specified, each value is approximate and each range of values included herein is inclusive of the end values defining the range. As used herein, unless otherwise noted, the term "set" means one or more (i.e., at least one) and the phrase "any solution" means any now known or later developed solution. Furthermore, as used herein, ultraviolet radiation/light means electromagnetic radiation having a wavelength ranging from approximately 10 nanometers (nm) to approximately 400 nm, while ultraviolet-C (UV-C) means electromagnetic radiation having a wavelength ranging from approximately 100 nm to approximately 280 nm, ultraviolet-B (UV-B) means electromagnetic radiation having a wavelength ranging from approximately 280 to approximately 315 nanometers, and ultraviolet-A (UV-A) means electromagnetic radiation having a wavelength ranging from approximately 315 to approximately 400 nanometers.

As also used herein, a material/structure is "transparent" when the material/structure allows at least ten percent of radiation having a target wavelength, which is radiated at a normal incidence to an interface of the layer, to pass there through. Furthermore, as used herein, a material/structure is "reflective" when the material/structure has a reflection coefficient of at least thirty percent for radiation having a target wavelength. In a more particular embodiment, a material/structure is "highly reflective" when the material/structure has a reflection coefficient of at least eighty percent for radiation having a target wavelength. In an embodiment, the target wavelength of the radiation corresponds to a wavelength of radiation emitted or sensed (e.g., peak wavelength+/−five nanometers) by an active region of an optoelectronic device during operation of the device. For a given layer, the wavelength can be measured in a material of consideration and can depend on a refractive index of the material.

Aspects of the invention provide a solution in which surface(s) are sterilized using ultraviolet radiation. To this extent, the ultraviolet radiation can be directed at the surface(s) in such a manner as to harm (e.g., suppress growth of, reduce an amount of, kill, damage, injure, etc.) any organisms that may be present on the surface(s). The organism(s) can comprise any combination of various types of organisms, such as bacteria, viruses, protozoa, biofilms, mold, and/or the like. The discussion herein refers to the sterilization of one or more surfaces. As used herein, "sterilizing" and "sterilization" refer to harming one or more target organisms, and include purification, disinfection, sanitization, and/or the like. Furthermore, as used herein a "sterilized surface" includes a surface that is devoid of any live organisms, a surface that is devoid of any live targeted organisms (but which may include non-targeted organisms), and a surface that includes some live targeted organism(s), but which is substantially free of such organism(s).

Figure 1:
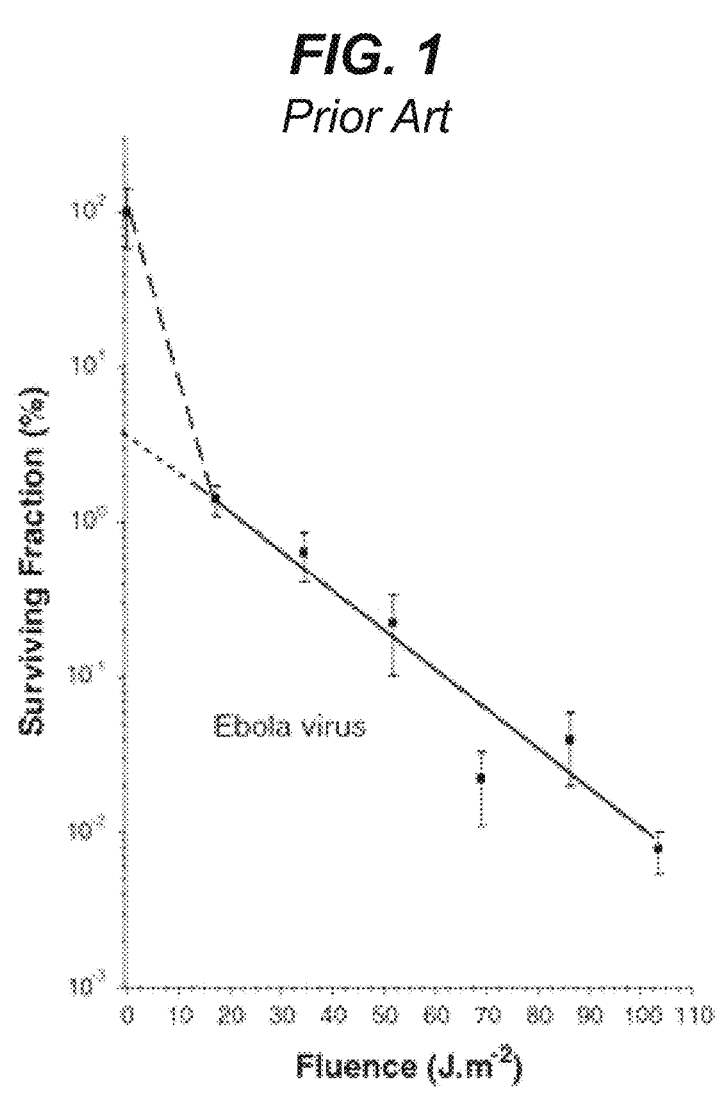

In an embodiment, a beam of ultraviolet radiation is utilized to deliver a target dose of ultraviolet radiation to a target surface area. It is understood that the target dose can vary based on the type of microorganism being targeted. For example, FIG. 1 shows a log reduction of the Ebola virus as a function of radiative dose according to the prior art. However, it is understood that the radiative dose required to achieve a comparable level of reduction varies based on the target microorganism. Illustrative target doses of ultraviolet radiation include: 3-5 $mJ/cm^2$ for Ebola virus; 6-12 $mJ/cm^2$ for *E-coli*; and 38 $mJ/cm^2$ for *Clostridium difficile* bacteria. However, embodiments can include different doses, which can be selected based on a higher desired log reduction and/or a surface on which the contaminant is present. For example, in another embodiment, the dose is selected to provide a 6 log reduction of the corresponding contaminant. To this extent, embodiments can use higher doses, such as 5-20 $mJ/cm^2$ for the Ebola virus.

The radiation power utilized should be sufficient to deliver the target dose of ultraviolet radiation within a target amount of time. The target amount of time can vary based on the particular application. In an embodiment, the target amount of time is less than or equal to approximately one minute for an embodiment in which the ultraviolet radiation is delivered within a chamber. In another embodiment, the target amount of time is less than or equal to five seconds when the ultraviolet radiation is delivered using a handheld device. However, it is understood that higher times are possible. In an embodiment, the time is any duration up to ten minutes. To ensure the target area receives at least the target dose, the beam of ultraviolet radiation can have only a reasonable variation in intensity. In an embodiment, the beam of ultraviolet radiation has a variation in intensity of less than forty percent across a surface area being illuminated. In a more particular embodiment, the beam of ultraviolet radiation varies by less than twenty percent across the surface area being illuminated.

Overview of Protective System

In an embodiment, a system for protecting a user from inadvertent exposure to contaminant(s), such as a bacterial or viral pathogen, a chemical contaminant, and/or the like, includes multiple systems, which can be cooperatively utilized to keep the user protected. To this extent, FIG. 2 shows a high level diagram of an illustrative protection system 10 according to an embodiment. The protection system 10 includes various components, each of which performs one or more functions to protect the user 2 from exposure to a harmful substance present or potentially present in an environment 4 within which the user 2 is located. As illustrated, the protection system 10 can include three main components, a supervisor 12, a protective suit 14, and a decontamination system 16, each of which is described further herein. However, it is understood that embodiments can include additional or fewer components. For example, an embodiment provides only the protective suit 14, another embodiment provides only the decontamination system 16, and still another embodiment provides only the protective suit 14 and the decontamination system 16. Additional components that can be implemented in a protection system 10 can include systems/personnel for treating an inadvertent exposure, containing a leak/spill, securing the environment 4, and/or the like. While shown and described in conjunction with a single user 2, protective suit 14, and decontamination system 16, it is understood that embodiments can include any number of users 2, protective suits 14, and/or decontamination systems 16 described herein.

In general, the user 2 puts on the protective suit 14 prior to entering the environment 4. While located within the environment 4, the protective suit 14 can be configured to completely isolate the user 2 from exposure to contaminant(s) located in or possibly located within the environment 4. The protective suit 14 can include a component (e.g., a computing device) capable of communicating with a supervisor 12, which can be a computer system, an individual, and/or the like. For example, the protective suit 14 can be configured to report the status, including any failures, of one or more of the protective subsystems incorporated in the protective suit 14 to the supervisor 12. The supervisor 12 may direct the user 2 to exit the environment 4 and enter the decontamination system 16 in response to any type of event, such as a time period expired, a failure of a subsystem of the protective suit 14, a condition of the user 2 (self-reported or detected by the protective suit 14), and/or the like. Alternatively, the user 2 can exit the environment 4 and enter the decontamination system 16 without direction from the supervisor 12, e.g., after completing a shift, completing a task, in response to an event, and/or the like.

The decontamination system 16 can be configured to sterilize various surfaces of the protective suit 14 prior to the user 2 removing the protective suit 14. For example, the decontamination system 16 can include a handheld device for sterilizing smaller areas of the protective suit 14, e.g., areas near seams opened when the protective suit is removed. Furthermore, the decontamination system 16 can include a chamber with one or more components operable to sterilize substantially all of the protective suit 14. For example, the chamber can include a shower, one or more ultraviolet sources, a feedback component (e.g., a fluorescent sensor), and/or the like, which can be operated by a computer system to sterilize the protective suit 14. During a decontamination process, the supervisor 12 can monitor data acquired by the protective suit 14 and/or the decontamination system 16 to determine whether the decontamination process is complete. Additionally, the supervisor 12 can communicate with the user 2 (e.g., via a communications system incorporated into the protective suit 14 and/or the decontamination system 16) to receive information regarding the condition of the user 2. Once the user 2 and/or the supervisor 12 are satisfied that the protective suit 14 is fully sterilized, the user 2 can remove the protective suit 14 and exit the decontamination system 16 outside of the environment 4.

In an illustrative embodiment, the supervisor 12 can have the authority to restrict exit of the user 2 from the decontamination system 16 depending on, for example, biological data collected from the user 2. For example, if the user 2 shows the signs of sickness (such as fever or other characteristic symptoms) the supervisor 12 may decide to isolate the user 2 and prohibit exit of the user 2 from the decontamination system 16. Alternatively, the user 2 can be redirected to a treatment facility without taking off the protective suit 14. The supervisor 12 can monitor the sterilization process and determine it is complete based on feedback data collected by the decontamination system 16. Additionally, it is understood that the user 2 and the decontamination system 16 also can communicate. For example, the decontamination system 16 can request that the user 2 change position within a chamber, move one or more limbs, evaluate/sterilize a particular portion of the protective suit 14, report any symptoms, and/or the like.

Figure 3:
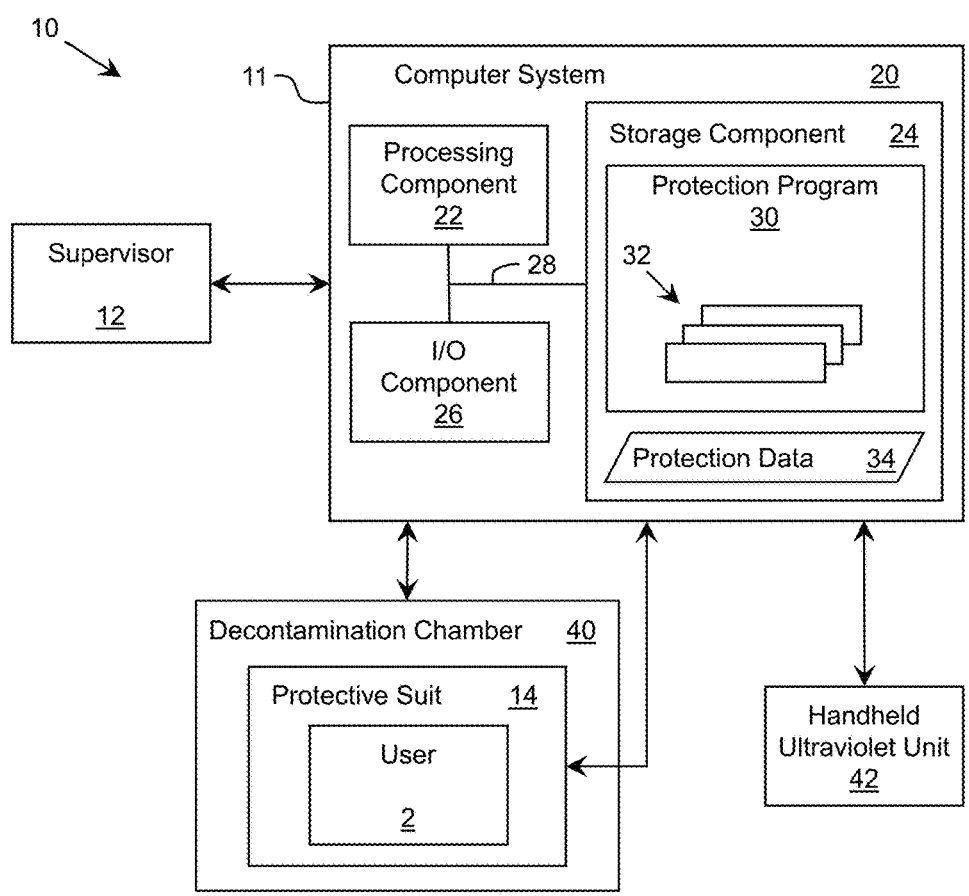

FIG. 3 shows a more detailed view of an illustrative protection system 10 according to an embodiment. In this case, the decontamination system 16 (FIG. 2) includes a monitoring and/or control system 11, a decontamination chamber 40, and a handheld ultraviolet unit 42. However, it is understood that these are only illustrative of various components and system that can be implemented as part of a decontamination system 16 described herein. Additionally, it is understood that a decontamination system 16 described herein may not include one or more of the components and systems shown and described in conjunction with FIG. 3. Regardless, in FIG. 3, the user 2 is shown located within the decontamination chamber 40 of the protection system 10. The monitoring and/or control system 11 is shown implemented as a computer system 20 that can perform a process described herein in order to protect one or more users 2 from exposure to a harmful substance, such as a chemical or biological hazard present or potentially present in an environment. In particular, the computer system 20 is shown including a protection program 30, which makes the computer system 20 operable to treat the surface(s) of the protective suit 14 worn by the user 2 with ultraviolet radiation by performing a process described herein.

The computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, the processing component 22 executes program code, such as the protection program 30, which is at least partially fixed in storage component 24. While executing program code, the processing component 22 can process data, which can result in reading and/or writing transformed data from/to the storage component 24 and/or the I/O component 26 for further processing. The pathway 28 provides a communications link between each of the components in the computer system 20. The I/O component 26 can comprise one or more human I/O devices, which enable a human supervisor 12 to interact with the computer system 20 and/or one or more communications devices to enable a supervisor system 12 to communicate with the computer system 20 using any type of communications link. To this extent, the protection program 30 can manage a set of interfaces (e.g., graphical user interface(s), application program interface, and/or the like) that enable human and/or system supervisors 12 to interact with the protection program 30. Furthermore, the protection program 30 can manage (e.g., store, retrieve, create, manipulate, organize, present, etc.) the data, such as protection data 34, using any solution.

In any event, the computer system 20 can comprise one or more general purpose computing articles of manufacture (e.g., computing devices) capable of executing program code, such as the protection program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the protection program 30 can be embodied as any combination of system software and/or application software.

Furthermore, the protection program 30 can be implemented using a set of modules 32. In this case, a module 32 can enable the computer system 20 to perform a set of tasks used by the protection program 30, and can be separately developed and/or implemented apart from other portions of the protection program 30. As used herein, the term "component" means any configuration of hardware, with or without software, which implements the functionality described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 20.

When the computer system 20 comprises multiple computing devices, each computing device can have only a portion of the protection program 30 fixed thereon (e.g., one or more modules 32). However, it is understood that the computer system 20 and the protection program 30 are only representative of various possible equivalent computer systems that may perform a process described herein. To this extent, in other embodiments, the functionality provided by the computer system 20 and the protection program 30 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 11 can be implemented without any computing device, e.g., using a closed loop circuit implementing a feedback control loop in which the outputs of one or more sensing devices are used as inputs to control the operation of one or more other devices. Illustrative aspects of the invention are further described in conjunction with the computer system 20. However, it is understood that the functionality described in conjunction therewith can be implemented by any type of monitoring and/or control system 11.

Regardless, when the computer system 20 includes multiple computing devices, the computing devices can communicate over any type of communications link. Furthermore, while performing a process described herein, the computer system 20 can communicate with one or more other computer systems using any type of communications link. To this extent, while not shown for clarity, it is understood that the decontamination chamber 40, protective suit 14, handheld ultraviolet unit 42, and/or supervisor 12 can comprise a computer system configured as described in conjunction with the computer system 20. Regardless, the communications link can comprise any combination of various types of optical fiber, wired, and/or wireless links; comprise any combination of one or more types of networks; and/or utilize any combination of various types of transmission techniques and protocols.

As discussed herein, the protection program 30 enables the computer system 20 to treat surface(s) of the protective suit 14. To this extent, the computer system 20 can operate one or more ultraviolet radiation sources included in the protective suit 14, the decontamination chamber 40, the handheld ultraviolet unit 42, and/or the like, to direct ultraviolet radiation onto one or more surfaces of the protective suit 14 in order to sanitize the surface(s). Furthermore, the computer system 20 can receive feedback data regarding a surface of the protective suit 14 from feedback component(s) incorporated in the protective suit 14, the decontamination chamber 40, the handheld ultraviolet unit 42, and/or the like, which can include one or more sensing devices for acquiring data regarding the surface of the protective suit 14 using any solution. In an embodiment, the protection system 10 includes control component(s), power component(s), control logic, and/or the like, capable of being implemented and operated in various different operating configurations, such as: contamination detection, during which a presence and/or location of a contaminant is determined; sterilization, during which identified contaminants are sterilized; and sterilization confirmation, during which the sterilization of contaminated areas is confirmed.

Figure 4:
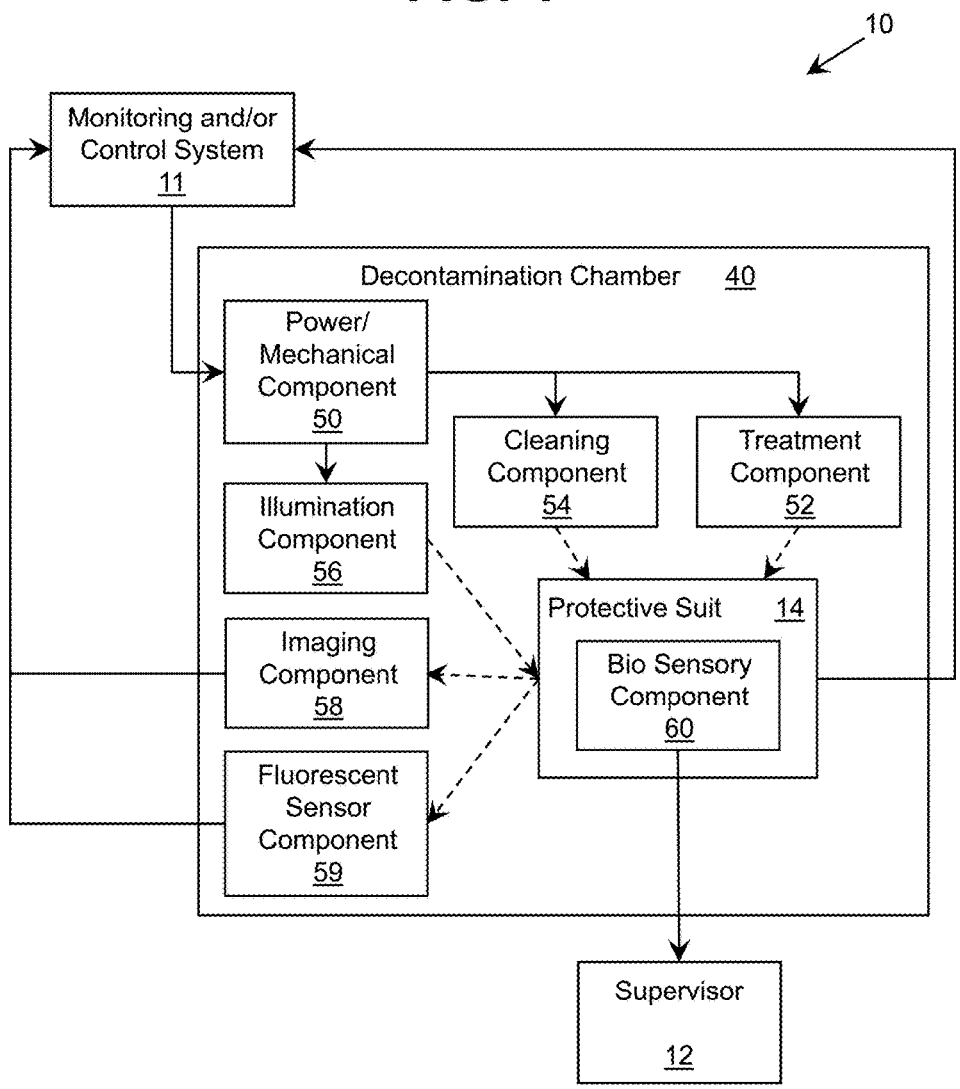

Regardless, the monitoring and/or control system 11 can operate and/or receive protection data 34 from various devices incorporated in the protective suit 14, the decontamination chamber 40, the handheld ultraviolet unit 42, and/or the like, in order to sterilize the protective suit 14 using a process described herein. To this extent, FIG. 4 shows a component-level view of an illustrative protection system 10 according to an embodiment. In this case, a handheld ultraviolet unit 42 (FIG. 3) is not shown implemented as part of the protection system 10.

As illustrated, the monitoring and/or control system 11 receives protection data 34 (FIG. 3) from various components in the decontamination chamber 40 and can operate a power/mechanical component 50 of the decontamination chamber 40. while the monitoring and/or control system 11 is shown implemented apart from the decontamination chamber 40, it is understood that an embodiment of the decontamination chamber 40 can include the monitoring and/or control system 11. Regardless, the power/mechanical component 50 can adjust the operation of various components in the decontamination chamber 40 based on control signals/data received from the monitoring and/or control system 11. To this extent, the power/mechanical component 50 can be configured to distribute appropriate power and/or control signals to devices included in: a treatment component 52 (e.g., one or more ultraviolet light sources); a cleaning component 54 (e.g., one or more shower heads for liquid sources, such as water and/or chemical substances); an illumination component 56 (e.g., visible and/or ultraviolet light source(s)); an imaging component 58 (e.g., visible and/or ultraviolet camera(s)); and a fluorescent sensor component 59.

For example, the power/mechanical component 50 can adjust the temporal-power schedule of these device(s) and/or the wavelength-power schedule of light sources in response to the control data/signals received from the monitoring and/or control system 11. As used herein, temporal-power schedule refers to a distribution of power among devices (e.g., sources of light) as a function of time, whereas wavelength-power schedule refers to distribution of power among sources of light as a function of the wavelength(s) of light emitted by these sources. To this extent, the power/mechanical component 50 can coordinate the actions of a set of shower heads in the cleaning component 54 in order to provide a temporal and spatial schedule of disbursement of liquids as defined by the monitoring and/or control system 11. Additionally, the power/mechanical component 50 can control ultraviolet radiation emitted from the treatment component 52 to sterilize substantially all of an outer surface area of the protective suit 14.

In an embodiment, the decontamination chamber 40 is configured with one or more components for providing information to ensure that the protective suit 14 is efficiently and/or thoroughly cleaned. For example, the decontamination chamber 40 can enable the detection of shadows present within the chamber, which can reduce an efficiency of the ultraviolet sterilization. In an embodiment, the illumination component 56 includes visible light source(s) positioned and directed within the decontamination chamber 40 similar to the ultraviolet source(s) of the treatment component 52 (e.g., co-located). The power/mechanical component 50 can operate the visible light source(s) in the illumination component 56 and/or imaging device(s) in the imaging component 58 to acquire image data for analysis by the monitoring and/or control system 11. In an embodiment, the monitoring and/or control system 11 can instruct the power/mechanical component 50 to adjust one or more aspects of the illumination component 56 in order to reduce and/or eliminate the shadow regions. Illustrative adjustments include adjusting the power and/or orientation (e.g., by angular rotation and/or relocation) of one or more of the visible light source(s). The monitoring and/or control system 11 can store data regarding the adjustments (e.g., as protection data 34 of FIG. 3) and use the adjustment data to make similar adjustments to the ultraviolet source(s) of the treatment component 52 as part of sterilizing the outer surface of the protective suit 14.

During a sterilization process, the power/mechanical component 50 can operate a set of ultraviolet source(s) in illumination component 56, which are configured to induce fluorescent signal(s) detected by sensor(s) in the fluorescent sensor component 59. The fluorescent sensor component 59 can forward data regarding the detected fluorescent signal(s) for processing and use by the monitoring and/or control system 11 during the sterilization process. In an embodiment, the illumination component 56 includes visible light source(s) positioned and directed within the decontamination chamber 40 similar to the ultraviolet source(s) of the illumination component 56. The power/mechanical component 50 can operate the visible light source(s) in the illumination component 56 and/or imaging device(s) in the imaging component 58 to acquire image data for analysis by the monitoring and/or control system 11. In an embodiment, the monitoring and/or control system 11 can instruct the power/mechanical component 50 to adjust one or more aspects of the illumination component 56 in order to reduce and/or eliminate the shadow regions. The monitoring and/or control system 11 can store data regarding the adjustments (e.g., as protection data 34) and use the adjustment data to make similar adjustments to the ultraviolet source(s) of the illumination component 56 as part of the sterilization process. To this extent, the monitoring and/or control system 11 can adjust one or more aspects of a showering schedule, an ultraviolet radiation schedule, and/or the like.

While described as being included in separate components 52, 56, it is understood that the ultraviolet source(s) used for sterilizing the protective suit 14 and the ultraviolet source(s) used to induce fluorescent signal(s) can be the same ultraviolet sources. For example, the power/mechanical component 50 can adjust one or more aspects of operation of an ultraviolet source based on its use. To this extent, an ultraviolet source can be configured to be operated in an ultraviolet sterilizing mode, during which the ultraviolet source is operated at high power, and an ultraviolet fluorescent inducing mode, in which the ultraviolet source is operated at a lower power and/or different emission wavelength. The wavelength can be tuned, for example, using an ultraviolet source including an array of ultraviolet emitting devices having different wavelengths, and selecting the ultraviolet emitting device(s) within the array having the desired wavelength(s).

It is understood that a decontamination chamber 40 can include various other components. For example, the decontamination chamber 40 can include one or more components for interfacing with the user 2 (FIG. 3) located within the protective suit 14. To this extent, such components can include a set of input ports and/or a remote control mechanism, which can enable the user 2 to affect the operation of one or more components of the decontamination chamber 40. Additionally, the interface can include an audio and/or visual presentation of the progress and/or results of the sterilization process, e.g., via a screen, speakers, and/or the like. The decontamination chamber 40 also can include an air blowing capability for drying the protective suit 14, wiping the mask of the protective suit 14, and/or the like. Additionally, when within the chamber, the protective suit 14 can be connected to the power/mechanical component 50 to receive power for recharging and/or operating one or more components of the protective suit 14, acquiring data from one or more components of the protective suit 14, and/or the like. In an embodiment, the protective suit 14 includes a bio sensory component 60, which includes a set of sensors for acquiring biometric data regarding the user 2, such as a body temperature, a blood pressure, a pulse, perspiration, and/or the like. The biometric data can be provided to the monitoring and/or control system 11 and/or presented to the user 2 and/or a supervisor 12 for use in determining an overall health of the user 2.

Decontamination Chamber

As described herein, embodiments provide a decontamination chamber 40 for sterilizing a protective suit 14, e.g., prior to the user 2 removing the protective suit 14. Furthermore, such a decontamination chamber 40 can be utilized to sterilize the user 2 (e.g., body and/or clothing) him/herself, e.g., after suspected or actual exposure to a contaminant. As described herein, the chamber 40 can incorporate any combination of various features to sterilize the protective suit 14 or user 2, including a shower, ultraviolet sources, as well as components for detecting the presence and/or location of contaminants. While primarily shown and described in conjunction with disinfection of a protective suit 14 and/or user 2, it is understood that a chamber 40 described herein can be configured and utilized to sterilize any article placed there within.

Figure 5:
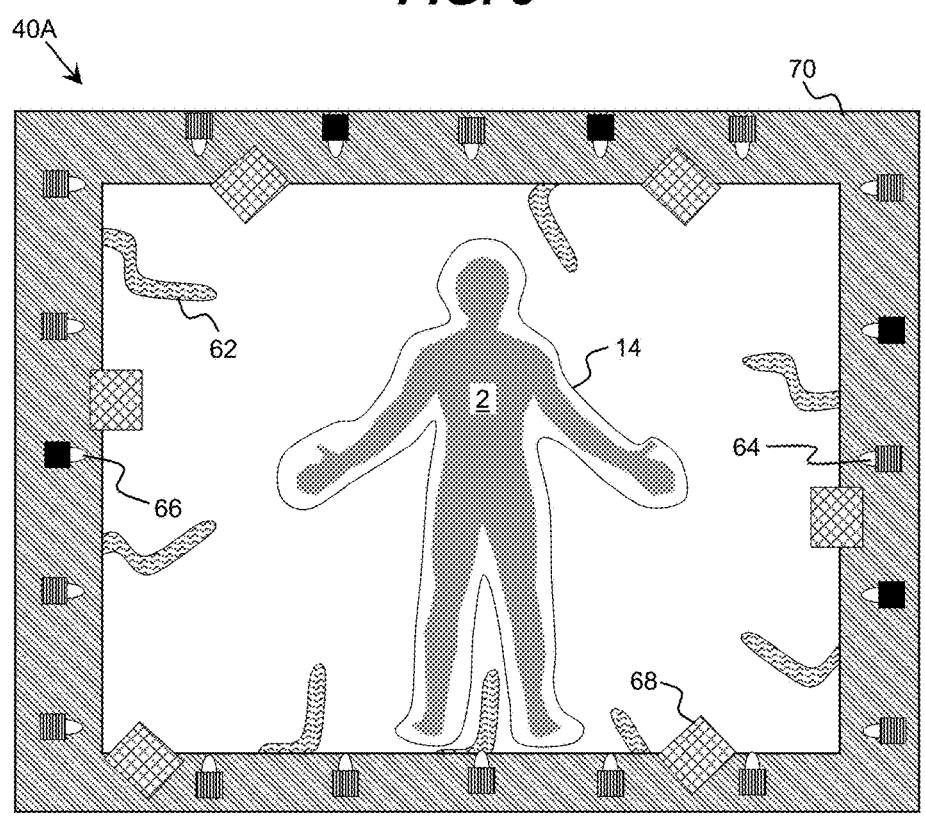

FIG. 5 shows an illustrative decontamination chamber 40A according to an embodiment. In this case, the decontamination chamber 40A includes multiple shower heads 62 (e.g., implemented as part of a cleaning component 54), multiple ultraviolet disinfection sources 64 (e.g., implemented as part of a treatment component 52), multiple ultraviolet fluorescent sources 66 (e.g., implemented as part of a fluorescent sensor component 59), and multiple cameras 68 (e.g., implemented as part of an imaging component 58) capable of capturing fluorescent radiation.

It is understood that various ultraviolet sources 64, 66 can be employed for disinfection and/or fluorescent signal induction. Illustrative ultraviolet sources 64, 66 include an ultraviolet light emitting diode (LED), an array of two or more ultraviolet LEDs, a mercury lamp, and/or any combination thereof. The ultraviolet sources 64, 66 can include multiple ultraviolet emitting devices of differing wavelengths, which can be operated at different intensity levels and/or time schedules to implement a sterilization process described herein. In an embodiment, the ultraviolet disinfection source 64 is configured to provide optimal sterilization of a target biological agent, while the ultraviolet fluorescent source 66 is configured to provide optimal fluorescent signal generation of the target biological agent. In each case, the configuration can include selection of a primary wavelength of the ultraviolet radiation, an intensity of the ultraviolet radiation, a dose of the ultraviolet radiation, and/or the like.

Furthermore, the ultraviolet sources 64, 66 can include any combination of ultraviolet sources emitting focused beams, diffused light, and/or the like, and any combination of ultraviolet sources that are fixed or movable (e.g., rotatable and/or relocatable) within the decontamination chamber 40A. In an embodiment, at least some of the ultraviolet sources 64, 66 emit a focused beam of ultraviolet radiation that is movable along a surface of the protective suit 14. In this case, an ultraviolet disinfection source 64 can be utilized to sterilize a particular location on the protective suit 14, and an ultraviolet fluorescent source 66 can be utilized to identify the target area.

Figure 6A:
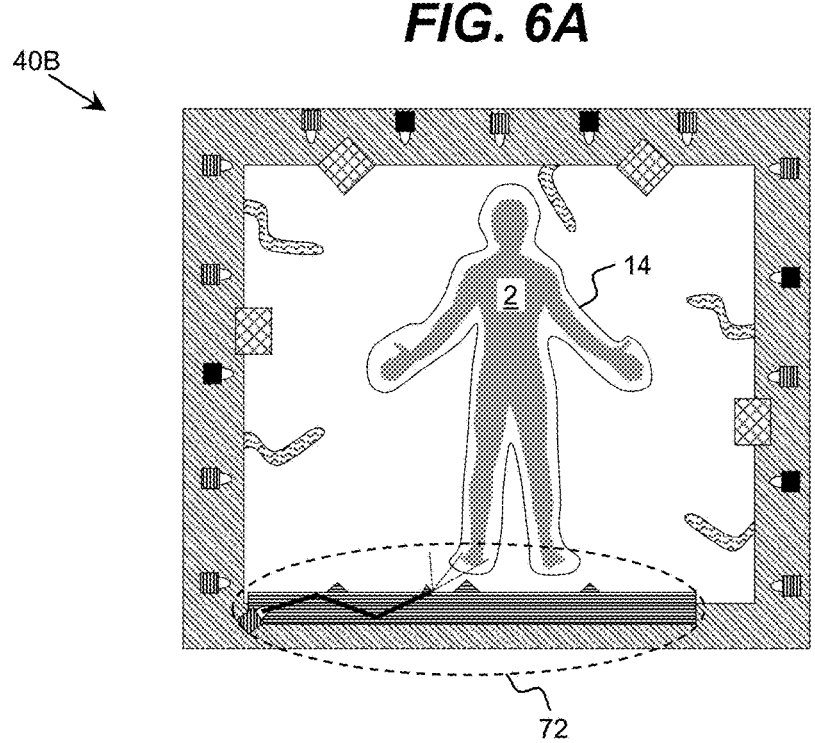
Figure 6B:
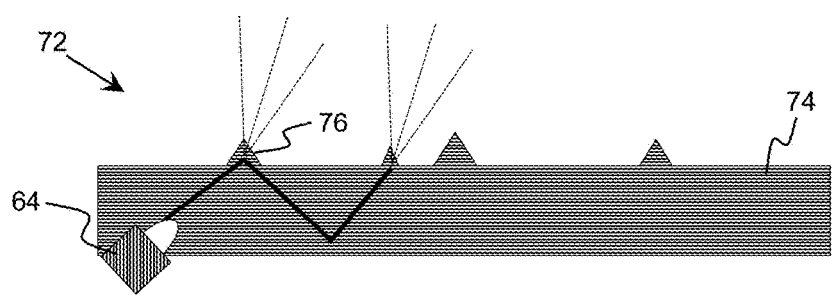

Furthermore, one or more of the ultraviolet sources 64, 66 can be coupled to and/or include a light guiding structure. For example, FIGS. 6A and 6B show another illustrative decontamination chamber 40B according to an embodiment. In this case, the decontamination chamber 40B includes a diffusive ultraviolet source 72. As shown in FIG. 6B, the diffusive ultraviolet source 72 includes an ultraviolet disinfection source 64 coupled to a light guiding structure 74. The light guiding structure 74 includes a set of diffusive elements 76 located on a surface thereof, from which diffusive ultraviolet radiation is emitted. While only a single diffusive ultraviolet source 72 is shown located on a floor of the decontamination chamber 40B, it is understood that this is only illustrative, and any number of diffusive ultraviolet sources 72 can be located on any surface of the decontamination chamber 40B. Furthermore, it is understood that a diffusive light guiding structure 74 is only illustrative, and a light guiding structure 74 can provide any light guiding functionality including, for example, collimating the ultraviolet light.

Returning to FIG. 5, fabrication of an ultraviolet source 64, 66, a mechanism for moving the ultraviolet source 64, 66, and/or a light guiding structure can be performed using any solution. For example, illustrative light guiding structures are shown and described in U.S. patent application Ser. Nos. 14/853,057 and 14/853,014, both of which were filed on 14 Sep. 2015 and both of which are hereby incorporated by reference. A diffusive ultraviolet source 64, 66 is shown and described in U.S. patent application Ser. No. 14/853,075, filed on 14 Sep. 2015, which is hereby incorporated by reference. An illustrative movable ultraviolet source 64, 66 is shown and described in U.S. patent application Ser. No. 14/870,515, filed on 30 Sep. 2015, which is hereby incorporated by reference.

The user 2 is shown standing centrally within the decontamination chamber 40A in a position with his/her hands and legs placed apart. Such a position can allow for more efficient sterilization of the surface of the protective suit 14. To this extent, the decontamination chamber 40A is shown including various shower heads 62, ultraviolet disinfection sources 64, ultraviolet fluorescent sources 66, and cameras 68 arranged on various sides of the user 2 when the user 2 is located in the position to provide substantially complete coverage of the exterior surfaces of the protective suit 14. A particular arrangement of the various components 62, 64, 66, 68 can be implemented based on attributes of the decontamination chamber 40A, the protective suit 14, and operational attributes of the components 62, 64, 66, 68, using any solution. Furthermore, it is understood that the decontamination chamber 40A can include one or more mechanisms for assisting the user 2 in standing in a correct location. Such mechanisms can include markings on the floor where the user 2 should stand, visible/audible instructions of any change in position required of the user 2 (e.g., which can be presented to the user 2 by the monitoring and/or control system 11 in response to analysis of video data acquired by one or more of the cameras 68), and/or the like.

The decontamination chamber 40A can be configured to facilitate the containment and/or efficient propagation of ultraviolet radiation therein as part of a sterilization process. To this extent, the decontamination chamber 40A can include an entrance and an exit, which can be closed to contain the ultraviolet radiation therein. For example, the entrance can be located within or near the environment 4 (FIG. 2) while the exit can be located outside/further away from the environment 4. In an embodiment, the decontamination chamber 40A can prevent operation of the ultraviolet source(s) therein until each entrance/exit is determined as being closed.

In an embodiment an interior surface of one or more of the walls and/or doors of the decontamination chamber 40A is defined by an ultraviolet transparent material 70. In this case, some or all of the ultraviolet sources 64, 66 can be embedded within the ultraviolet transparent material 70. Any suitable type of ultraviolet transparent material can be utilized. Illustrative materials include: fluorinated ethylenepropylene (EFEP), fluorinated ethylene propylene (FEP), perfluoroalkoxy (PFA), tetrafluoroethylene hexafluoropropylene vinylidene fluoride (THV), polytetrafluoroethylene (PTFE), polyvinylidene fluoride (PVDF), ethylene-tetrafluoroethylene (ETFE), ethylene chlorotrifluoroethylene (ECTFE), polychlorotrifluoroethene (PCTFE), a copolymer of tetrafluoroethylene and perfluoromethylvinylether (MFA), low density polyethylene (LDPE), perfluoroether (PFA), an amorphous fluoroplastic (e.g., Teflon AF), and/or the like. While primarily described in conjunction with fluoropolymers, it is understood that other comparable materials can be utilized. Illustrative materials include polylactide (PLA), fused silica, sapphire, THE, and/or the like. Additionally, one or more interior surfaces of the decontamination chamber 40A and/or a surface of one or more components exposed to the ambient (e.g., an exposed surface of the shower heads 62) can include a photo-catalyst, such as titanium oxide ($TiO_2$), copper, silver, and/or the like, which can induce disinfection of the corresponding surface and/or in the ambient of the interior of the decontamination chamber 40A.

An illustrative sterilization process performed using the decontamination chamber 40A can include the user 2 first entering the decontamination chamber 40A, closing any entrances/exits to the decontamination chamber 40A, and requesting initiation of the sterilization process (e.g., using an interface such as a start button, and audible command, and/or the like). A first stage of the sterilization process can include a thorough wash of the protective suit 14 using the shower heads 62. For example, the wash can utilize water and soap solutions, and can include multiple cycles of high pressure wash, different types of soaps, and/or one or more disinfectant chemicals, such as hydrogen peroxide, ethanol, isopropyl alcohol, sodium hypochlorite, iodophor, quaternary ammonium compounds, peroxyacetic acid, acid-anionic compounds, and/or the like. A particular combination of soaps and/or disinfectant chemicals can be selected based on the targeted contaminants.

In an embodiment, the chamber 40A can be configured to provide a disinfection bath as part of the wash, in which the protective suit 14 is at least partially (e.g., at least five percent) submerged in a bath containing disinfection chemicals. For substantially complete submersion of the protective suit 14 and user 2, in a bath, the chamber 40A can include an air supply system to allow the user 2 to remain submerged for an extended period of time. Furthermore, the wash and/or protective suit 14 can be configured to improve an effectiveness of the ultraviolet radiation treatment. For example, an embodiment of the wash can cover at least a portion of the protective suit 14 with an ultraviolet photoactivated chemical, such as peracetic acid, titanium oxide, or the like. Alternatively, the protective suit 14 can include a permanent covering of such a chemical.

After the wash, the protective suit 14 can be irradiated with ultraviolet light emitted by the ultraviolet disinfection sources 64. The irradiation can utilize a set of target wavelengths and a duration typically required to sterilize a surface of the protective suit 14. The set of target wavelength and duration can be selected based on the target contaminant(s) using any solution.

After an initial wash/ultraviolet radiation cycle, the ultraviolet fluorescent sources 66 can be utilized and a fluorescence signal, if any, can be acquired by the cameras 68. Data acquired by the cameras 68 can be analyzed (e.g., by a human and/or by the monitoring and/or control system 11) to determine whether additional disinfection may be required. If so, a new wash and/or ultraviolet radiation cycle can be performed. Such a procedure can be repeated any number of times until no fluorescent signal is detected from any part of the surface of the protective suit 14. It is understood that each cycle can be varied from another cycle. For example, a subsequent cycle can utilize a different set of target wavelengths, a different duration, a different combination of soaps and/or disinfectant chemicals, and/or the like, from a previous cycle. Furthermore, it is understood that the user 2 can be required to reposition him/herself during a cycle or from one cycle to another. For example, the user 2 may be instructed to have the arms in a lower position during a cycle or a portion thereof, and have the arms raised during another cycle or portion thereof.

Figure 7:
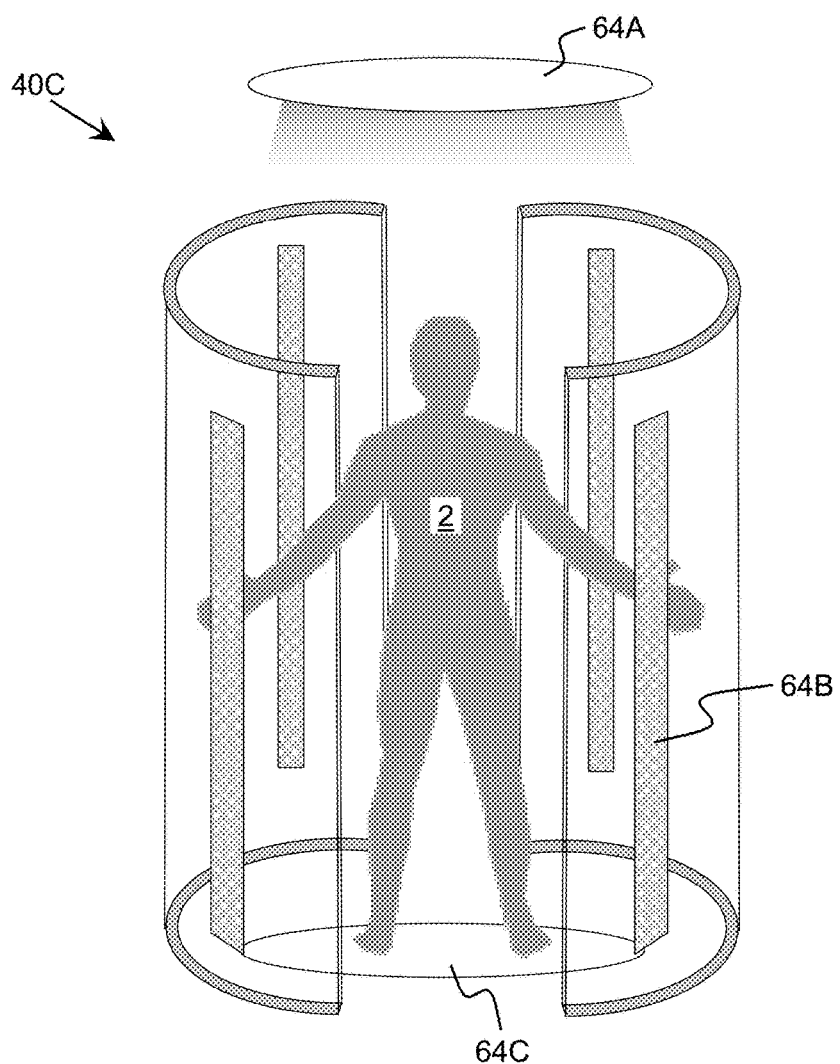

It is understood that various alternative configurations of decontamination chambers and sterilization processes are possible. For example, FIG. 7 shows still another illustrative decontamination chamber 40C according to an embodiment. As illustrated, the decontamination chamber 40C can include an arrangement of large ultraviolet disinfection sources 64A-64C, which can be utilized to sterilize substantially all of the user's 2 skin/clothing, rather than a protective suit worn by the user 2. Such a decontamination chamber 40C can be utilized, for example, where an inadvertent exposure to a contaminant is suspected, at a security checkpoint, a medical facility, and/or the like. While not shown, it is understood that the decontamination chamber 40C can further include one or more of visible light sources, cameras, ultraviolet fluorescent sources, fluorescent sensors, and/or the like, as described herein in order to ensure that substantially all of the user 2 has been irradiated.

Handheld Ultraviolet Unit

As discussed herein, an embodiment further provides a handheld ultraviolet unit 42 (FIG. 3), which can be utilized to sterilize localized portions of a surface of an object, such as an area of a protective suit 14 (FIG. 3), an area of the user 2, and/or the like, using ultraviolet radiation. In an embodiment, the handheld ultraviolet unit 42 can be configured to emit ultraviolet radiation having a total optical ultraviolet power of several hundred milliwatts. Such a power is sufficient to destroy viruses and bacteria using a slow movement of the handheld ultraviolet unit 42 above an area. In a more particular embodiment, the handheld ultraviolet unit 42 can be held a distance between a few millimeters to a few tens of centimeters above the area to be sterilized. The handheld ultraviolet unit 42 can be configured to deliver a required dose of ultraviolet radiation to sterilize an irradiated area within tens of seconds (e.g., sixty seconds) or less (e.g., in real time). In this manner, an entire area of an object, such as a protective suit 14 or the user 2, can be sterilized within a few minutes or less.

Figure 8:
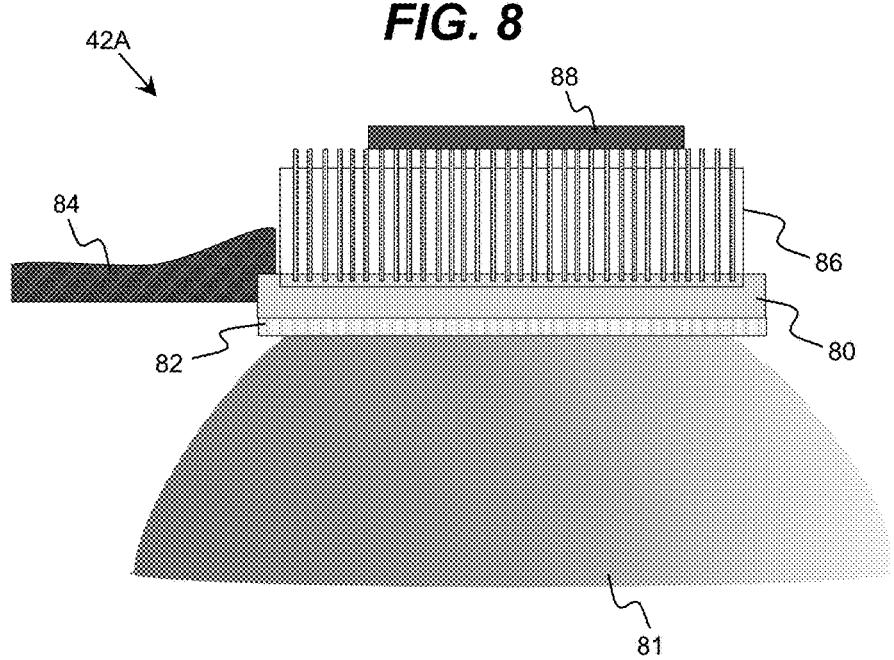

FIG. 8 shows an illustrative handheld ultraviolet unit 42A according to an embodiment. The handheld ultraviolet unit 42A can include an array of ultraviolet sources 80, which are configured to emit a beam of ultraviolet radiation 81. The array of ultraviolet sources 80 can include any combination of zero or more ultraviolet LEDs, zero or more mercury lamps, and/or the like. The handheld ultraviolet unit 42A also can include an optical element 82 located adjacent and optically coupled to the ultraviolet sources 80. The optical element 82 can comprise, for example, an ultraviolet transparent layer/region, a reflective layer/region, and/or the like, which can be configured to improve a uniformity or a collimation of the ultraviolet beam 81 emitted by the handheld ultraviolet unit 42A as well as provide protection of the array of ultraviolet sources 80 from the ambient environment. In an embodiment, the optical element 82 comprises a light guiding structure, which can be fabricated as described herein, e.g., from fluoropolymer materials. Regardless, the optical element 82, when included, can couple well with the light emitted by the array of ultraviolet sources 80. In an embodiment, the coupling ensures that at least fifty percent of the ultraviolet radiation emitted by the array of ultraviolet sources 80 enters the optical element 82. Furthermore, the optical element 82 can be configured to ensure that a loss of ultraviolet radiation within the optical element 82 is less than twenty percent.

A user can hold the handheld ultraviolet unit 42A to direct the ultraviolet beam 81 towards a surface to be sterilized. In general, motion of the handheld ultraviolet unit 42A will be necessary to sterilize an entire target area of surface of an object. The handheld ultraviolet unit 42A can include a handle 84 which can be utilized by a user to hold the handheld ultraviolet unit 42A close to the surface being sterilized and slowly move the handheld ultraviolet unit 42A, and as a result, the ultraviolet beam 81, along the surface. During operation, the array of ultraviolet sources 80 may generate a significant amount of heat. To this extent, the handheld ultraviolet unit 42A can further include a heat sink 86 and a fan 88, which can assist in dissipating the heat away from the array of ultraviolet sources 80. For example, the heat sink 86 and fan 88 can be configured to prevent a temperature of the array of ultraviolet sources 80 from increasing more than twenty degrees Celsius above the ambient temperature. However, it is understood that an embodiment of the handheld ultraviolet unit 42A can be implemented without a handle 82, heat sink 86, and/or fan 88.

It is understood that the handheld ultraviolet unit 42A can include various other devices. For example, the handheld ultraviolet unit 42A can include one or more of: a power source, such as a rechargeable battery; a mechanism for enabling a user to turn on/off the handheld ultraviolet unit 42A; a mechanism for providing feedback data to the user and/or a monitoring and/or control system 11 (FIG. 3) regarding operation of the device, sterilization of an area, and/or the like; a mechanism for detecting a distance to the surface; a mechanism for providing a visual indication of a location on the surface currently being irradiated by the ultraviolet beam 81 (e.g., a visible light source co-located with the ultraviolet sources 80); a mechanism for evaluating the surface for a presence of contaminant(s) (e.g., a fluorescent source/sensor); and/or the like. Additionally, the handheld ultraviolet unit 42A can include a mechanism, such as an illuminator attachment, a chemical disinfection component, and/or the like, which can be utilized to sterilize some or all of the surface of the handheld ultraviolet unit 42A.

Figure 9A:
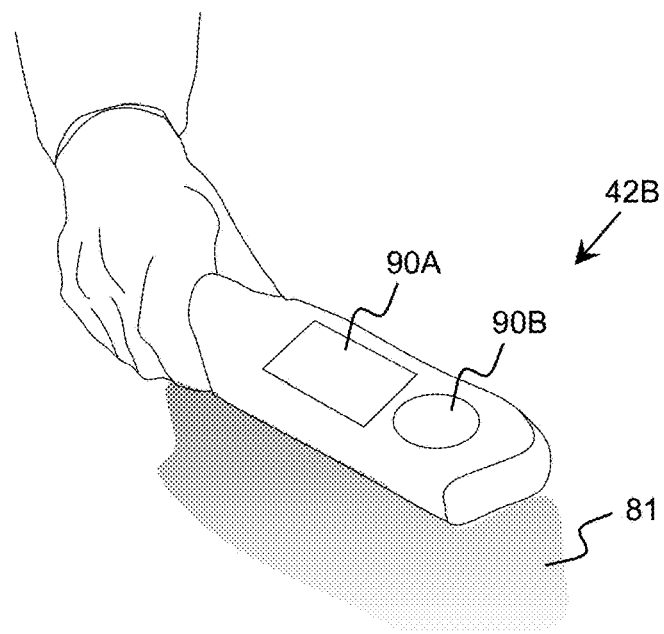
Figure 9B:
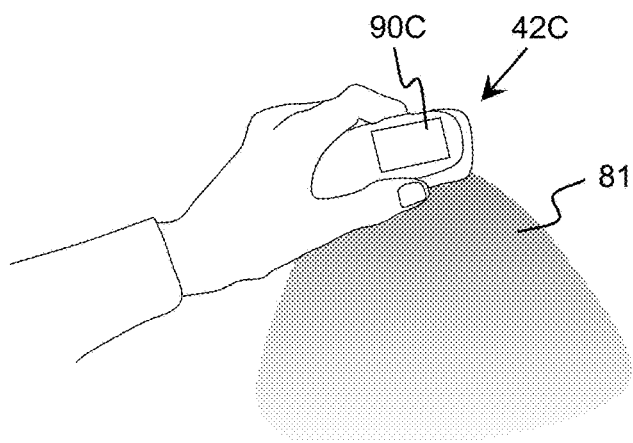

FIGS. 9A and 9B show illustrative handheld ultraviolet units 42B, 42C according to embodiments. As shown in FIG. 9A, the handheld ultraviolet unit 42B can be configured to be held similar to a wand, while in FIG. 9B, the handheld ultraviolet unit 42C can be configured to be held similar to a smart phone, or other type of mobile computing device, and could comprise a smart phone with an additional mechanism for generating ultraviolet radiation as described herein. Regardless, each handheld ultraviolet unit 42B, 42C is shown including a set of I/O domains 90A-90C, which enable operation of the unit 42B, 42C by a user. For example, domain 90A can comprise a liquid crystal display or similar type of screen for presenting information to the user, while domain 90B can comprise a set of buttons enabling the user to request operations. Alternatively, as shown in FIG. 9B, the domain 90C can comprise a touch screen, which can present information and receive instructions from the user in a manner similar to smart phones.

FIGS. 10A and 10B show front and side views, respectively, of an illustrative handheld ultraviolet unit 42D according to another embodiment. The handheld ultraviolet unit 42D includes an input screen 90D and an output screen 90E. The input screen 90D can be utilized by a user to specify any combination of various input parameters, such as, for example: optical properties of a surface being irradiated; an approximate distance to the surface; a duration for delivering the disinfection dose; an intensity of the ultraviolet source(s); a choice of wavelength for the ultraviolet irradiation; a choice and/or intensity of ultraviolet sources for emitting radiation to excite a fluorescent response; and/or the like. Furthermore, the input screen 90D can enable the user to select one or more attributes of components utilized to focus the ultraviolet beam, such as a distance between lenses used to focus the beam and the ultraviolet source(s). Still further, the user can use the input screen 90D to operate one or more other devices included in the handheld ultraviolet unit 42D, such as a visible light source, an infrared light source, and/or the like. In any event, the handheld ultraviolet unit 42D can provide feedback regarding the currently selected parameters, the current operational state of the device, a remaining battery life, and/or the like, via the output screen 90E using any solution. Regardless, it is understood that these operational parameters are only illustrative and various other operational parameters can be selected by the user.

An illustrative set of devices included in the handheld ultraviolet unit 42D and a corresponding arrangement of these devices are shown in FIG. 10B. In this case, the handheld ultraviolet unit 42D includes a fluorescence component 92, which can include both a set of ultraviolet sources for generating ultraviolet radiation for inducing fluorescence and a set of fluorescence sensing devices. Additionally, the handheld ultraviolet unit 42D can include a distance detector 94, which can determine a distance between the handheld ultraviolet unit 42D and a surface using any solution, e.g., a radar, an infrared distance sensor, and/or the like. The handheld ultraviolet unit 42D also can include a reflectometer 96, which can detect one or more optical characteristics of a surface.

A control unit 98 (e.g., a computer system) can operate the various devices, and receive and process data acquired by the various input components included in the devices to affect operation of a set of ultraviolet sources for sterilizing the surface. For example, based on data acquired by the distance detector 94 and the reflectometer 96, the control unit 98 can determine a target intensity and duration for operating the set of ultraviolet sources to deliver a required dose for sterilizing the surface. In an embodiment, the control unit 98 makes such a determination using modeling and/or experimental data stored as protection data 34 (FIG. 3) on the control unit 98. In an embodiment, the required dose corresponds to a dose determined to be sufficient to result in a log reduction of a target microorganism (e.g., bacteria or virus) that is or may be present on the surface. The experimental data can be collected regarding for log reduction of a target microorganism based on an intensity of the radiation at a surface and the optical properties of the surface. The intensity at the surface can be estimated based on the distance of the handheld ultraviolet unit 42D from the surface through, for example, collection of experimental data for different distances of the handheld ultraviolet unit 42D, modeling and analytical estimates, and/or the like. Furthermore, the control unit 98 can communicate data (e.g., using a wireless communications solution) regarding the surface or the operation of the handheld unit 42D to an external system, such as the monitoring and/or control system 11 and/or the supervisor 12 shown in FIG. 3. Such information can include data regarding the detection of a target contaminant, a location at which the target contaminant was detected (e.g., using data acquired by a location system incorporated therein, such as a global positioning system unit), whether the location was successfully sterilized, and/or the like.

Figure 11A:
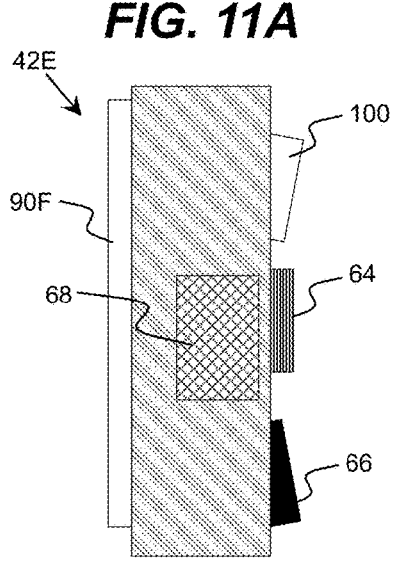
Figure 11B:
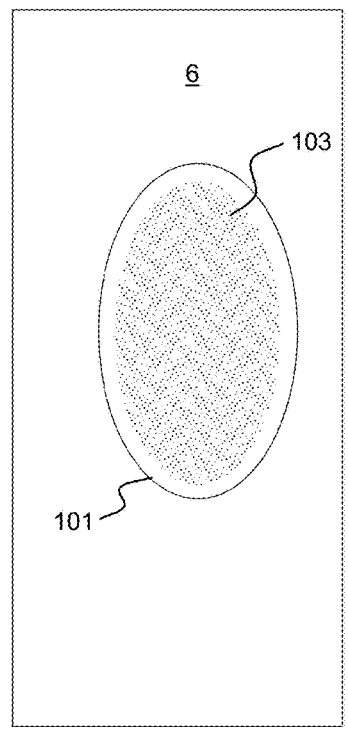

FIG. 11A shows a side view of an illustrative handheld ultraviolet unit 42E according to still another embodiment, and FIG. 11B illustrates illumination of a surface 6 by the handheld ultraviolet unit 42E. In this case, the handheld ultraviolet unit 42E is shown including an input/output interface 90F (e.g., a touch screen), a visible light source 100, an ultraviolet disinfection source 64, an ultraviolet fluorescent source 66, and a camera 68. In an embodiment, the visible light source 100 and ultraviolet sources 64, 66 can be configured to produce a comparable intensity distribution on a surface 6 that is a target distance away from the handheld ultraviolet unit 42E and have a comparable attenuation with distance from the handheld ultraviolet unit 42E to the surface 6. To this extent, as illustrated in FIG. 11B, an area 101 can be illuminated by the visible light source 100 and an area 103 can be illuminated by one or both of the ultraviolet sources 64, 66. In an embodiment, one or more of the sources 64, 66, 100 comprises a movable source as described herein, which can be rotated based on the distance to ensure that the areas 101, 103 continue to be substantially aligned on the surface 6. In an embodiment, the area 103 can have a size of at least approximately one square centimeter.

The camera 68 can detect an intensity of the visible light on the surface 6 and adjust operation of one or both of the ultraviolet sources 64, 66 in response to obtain a target level of ultraviolet radiation (e.g., dose). It is understood that a control unit 98 (FIG. 10B) included on the handheld ultraviolet unit 42E can adjust the level of ultraviolet radiation using any solution, such as adjusting an intensity of the ultraviolet radiation emitted, a duration of emitting the ultraviolet radiation, and/or the like. Upon completion of an ultraviolet radiation cycle (e.g., delivery of a target dose of ultraviolet radiation), the control unit 98 can provide an indication to the user, e.g., via the interface 90F, by blinking/turning off the visible light source 100, and/or the like. It is understood that a correlation between the intensity of the visible light and the ultraviolet intensity can be adjusted based on a set of optical properties of a surface 6 as the reflection and absorption of radiation can be different for different wavelengths of light.

As described herein, data regarding fluorescence can be utilized to attest whether the surface 6 contains contamination. Accordingly, the intensity of ultraviolet radiation generated by the ultraviolet disinfection source 64 can be adjusted based on the fluorescence data. It is understood that an ultraviolet fluorescent source 66 used to excite fluorescent radiation can have an operation wavelength in the ultraviolet spectra different from a wavelength of the ultraviolet disinfection source 64 used for sterilization of the surface 6. It is further understood that in some embodiments, an ultraviolet fluorescent source 66 also can be used to generate ultraviolet light for sterilization. In this case, the ultraviolet fluorescent source 66 can operate at different intensity levels and/or have a time periodic behavior. For example, the same ultraviolet source 64, 66 can alternate between an ultraviolet disinfection mode and an ultraviolet fluorescent mode.

It is understood that the various handheld ultraviolet units shown herein are only illustrative. To this extent, a handheld ultraviolet unit can include any combination of the various devices, interfaces, and mechanisms described herein. Furthermore, a handheld ultraviolet unit can include additional devices, interfaces, mechanisms not shown herein. For example, an embodiment of a handheld ultraviolet unit described herein can be configured only to detect a presence of a contaminant on a surface, e.g., using the fluorescence detection described herein, without being capable of generating a sufficient dose of ultraviolet radiation to sterilize the surface within a reasonable amount of time. In this case, the handheld ultraviolet unit can be utilized in conjunction with a sterilization solution, such as a decontamination chamber described herein.

Figure 12:
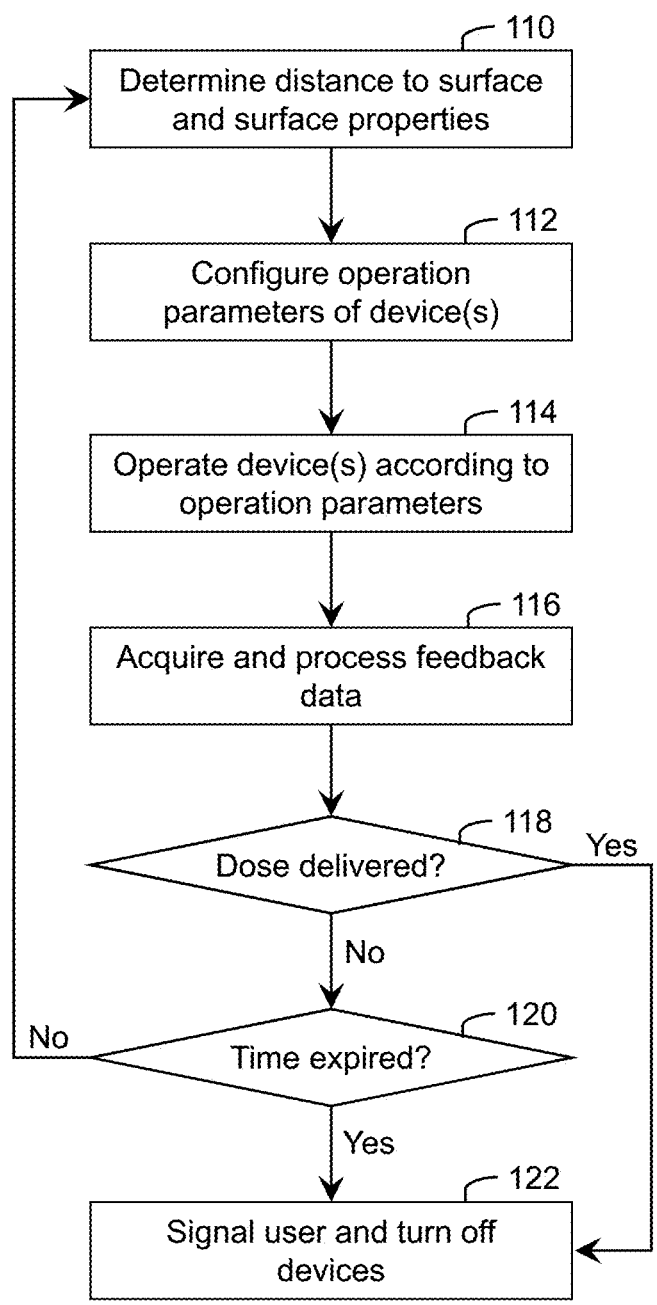

Regardless, FIG. 12 shows an illustrative process for sterilizing a surface, which can be performed using a handheld ultraviolet unit described herein, according to an embodiment. In action 110, the handheld ultraviolet unit 42 (FIG. 3), e.g., a computer system included therein, can determine a distance to the surface 6 (FIG. 3) and one or more properties of the surface. As part of determining the distance, the handheld ultraviolet unit 42 can generate an error and prompt the user of the handheld ultraviolet unit when the distance is outside of a target range of distances and/or no surface 6 is detected. In this case, the handheld ultraviolet unit 42 can periodically re-measure the distance until a surface is detected within the target range of distances. Furthermore, it is understood that the handheld ultraviolet unit 42 can generate a warning when the distance is approaching an extent of the target range of distances, in which case the process can proceed to the next action, or when the surface 6 has been moved outside of the target range of distances (e.g., too close or too far), in which case the process can remain in action 110. In the latter situation, the handheld ultraviolet unit 42 can signal the user and turn off the ultraviolet sources of the handheld ultraviolet unit 42, if necessary, until the surface 6 is again within range.

When the surface 6 is within the target range of distances from the handheld ultraviolet unit 42, in action 112, the handheld ultraviolet unit 42 can configure (e.g., set, adjust, or the like) the operation parameters for various source and acquisition devices located thereon based on the distance and/or one or more of the surface property(ies). For example, the operation parameters can include one or more of: on/off status of one or more of a visible light source, an ultraviolet source, an ultraviolet fluorescent source, a camera, a chemical source, and/or the like; duration and/or intensity of operation of the ultraviolet source(s), which can be determined based on a dose delivered and/or to be delivered; an intensity of an ultraviolet fluorescent source, a chemical source, a visible light source, and/or the like; etc. In an embodiment, the visible light sensed by the camera can provide feedback to adjust the intensity of the ultraviolet source. However, it is understood that one or more of the sources can be operated using a different operation schedule. For example, the chemical source may be a sprayer operated independently from the other sources, the ultraviolet fluorescent source can operate on a different schedule than the ultraviolet source and the visible source, and/or the like. In action 114, the handheld ultraviolet unit 42 can operate the various devices according to the operation parameters. Such operation can last for a predetermined minimum amount of time, such as one second.

In action 116, the handheld ultraviolet unit 42, e.g., a computer system included therein, can acquire and process feedback data regarding the operation of the device(s). The feedback data can include image data of the surface 6, data corresponding to a dose delivered to an area of the surface 6 (which can be calculated based on the intensity, duration, and distance data), data corresponding to a presence of a target contaminant on the surface 6, and/or the like. In action 118, the handheld ultraviolet unit 42 can determine whether a target dose has been delivered to the target area of the surface 6. Such a determination can be made based on an amount of ultraviolet radiation having illuminated the surface 6, a presence of the target contaminant on the surface 6, and/or the like. If not, the process can continue to action 120, in which the handheld ultraviolet unit 42 can determine whether an amount of time allocated for the sterilization process has expired. If not, the process returns to action 110 and continues in an iterative manner.

Once the dose has been delivered or the maximum time has expired, in action 122, the handheld ultraviolet unit 42 can signal the user and turn off the various devices. For example, the handheld ultraviolet unit 42 can indicate that the sterilization process has successfully completed or has timed out without successful completion. In response, the user can elect to start a new sterilization process, sterilize another surface 6 or area of the surface 6, and/or the like.

It is understood that the process of FIG. 12 is only illustrative, and various modifications are possible. For example, depending on the target surface 6, the optical properties of the surface 6 can be determined once at the beginning of a sterilization process, and not repeatedly during the process. Furthermore, an illustrative process can be implemented without acquiring and processing feedback data. For example, the handheld ultraviolet unit 42 can enable the user to input only a few relevant parameters, such as a type of surface 6 (e.g., skin, clothing, absorbent, reflective, transparent, and/or the like), a type of target contaminant (e.g., virus, bacteria, chemical, and/or the like), an approximate distance to the surface 6, and an amount of time desired for the sterilization. Subsequently, the handheld ultraviolet unit 42 can operate according to the input parameters and assume that the area has been successfully sterilized after completion of the process. The handheld ultraviolet unit 42 can further include an ability to provide feedback to the user regarding the area sterilized, such as an approximate size of the area, a visible indication of the area, and/or the like.

Protective Suit

As discussed herein, embodiments can be directed to the sterilization of a protective suit 14 (FIG. 2) worn by a user 2 (FIG. 2). The protective suit 14 can comprise any type of protective suit 14. An embodiment provides a protective suit 14 with one or more components configured to assist in the sterilization process and/or safety and comfort of the user 2. To this extent, an embodiment provides a protective suit 14 that is breathable, robust, and can be externally detoxified and/or detoxified using internal ultraviolet sources. In an embodiment, the protective suit 14 can be utilized in the protection system 10 (FIG. 1) as part of a coordinated system for sterilizing the suit 14.

Figure 13:
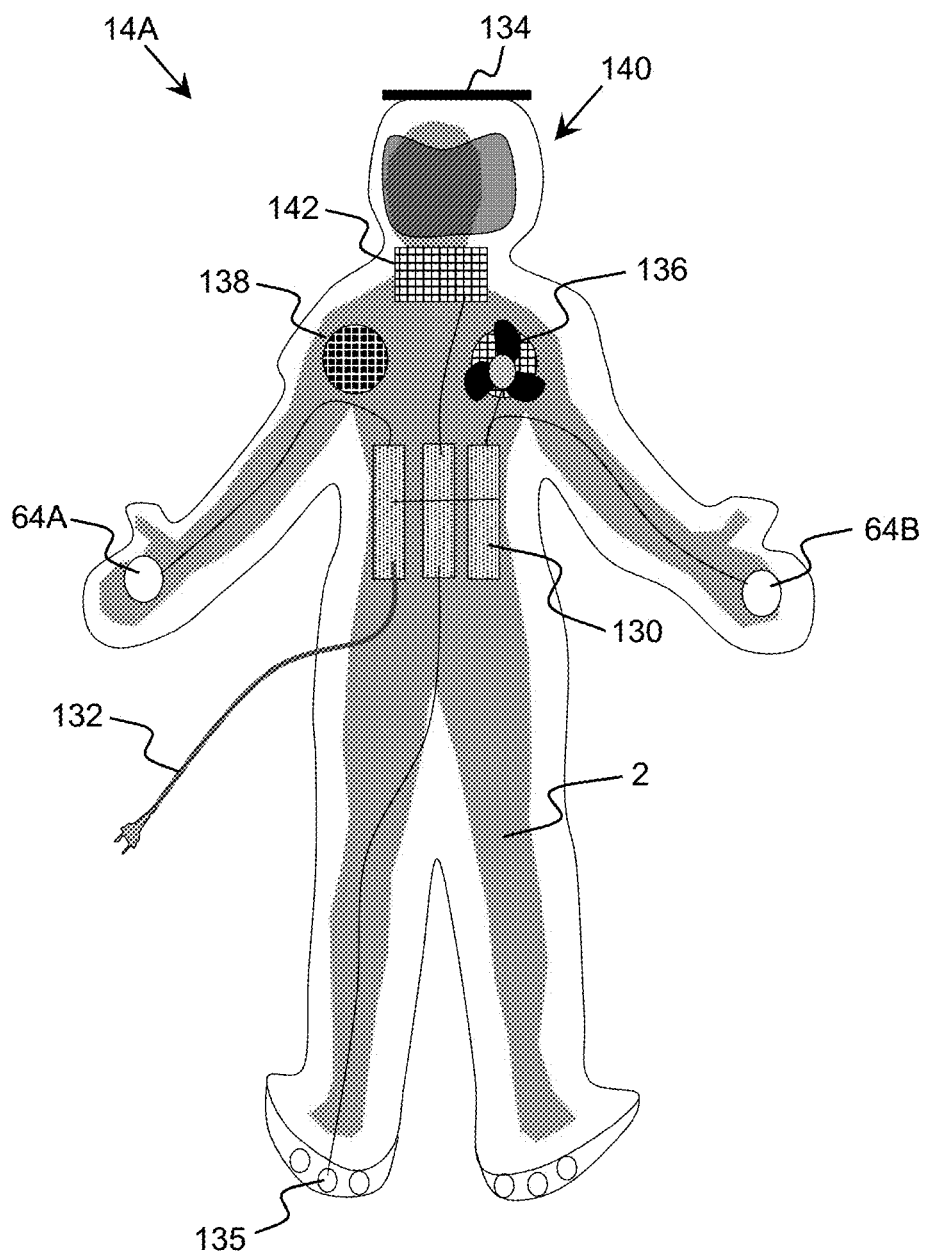

FIG. 13 shows an illustrative protective suit 14A according to an embodiment. The protective suit 14A can be fabricated of any material capable of withstanding ultraviolet radiation (e.g., impermeable to ultraviolet radiation), as well as being waterproof, resistant to tear, resistant to burning, and resistant to disinfection chemicals used for cleaning the protective suit 14A. Furthermore, the material of the protective suit 14A can be resistant to biohazards, such as bacteria or viruses. Illustrative materials include, for example, a polyethylene film combined with polypropylene non-woven filaments, or similar material suitable for protective garments, such as biohazard suits, chemical protective garments, and/or the like (e.g., Tychem® TK offered by DuPont). As the protective suit 14A described herein can include a combination of various electronic devices, the material of the protective suit 14A can further be configured to support the corresponding wiring required between a power source and the electrical device(s).

The protective suit 14A includes a power source, such as a set of rechargeable batteries 130. The batteries 130 can be configured to provide sufficient power for the various devices included in the protective suit 14A for a target length of time, which can be selected based on the corresponding environment and applications in which the protective suit 14A is to be utilized. The batteries 130 can be recharged using an electrical grid, e.g., access via an electrical connector 132. While the electrical connector 132 is shown extended from the protective suit 14A, it is understood that the protective suit 14A can include an area in which the electrical connector 132 can be secured from the ambient environment when not in use. Furthermore, an embodiment of the batteries 130 can be recharged using a wireless recharging solution. Additionally, an embodiment of the protective suit 14A can include a solar power unit 134, which can provide power and/or recharge the batteries 130, such as when access to the electrical grid is not convenient and/or during use of the protective suit 14A. While the solar recharging unit 134 is shown as being substantially flat and rigid, it is understood that such a unit can be fabricated from any lightweight and/or flexible material capable of converting solar light into an electrical current. It is understood that various alternative power sources are possible. For example, an embodiment of the protective suit 14A can include a set of biomechanical power generators 135 built into the shoes of the protective suit 14A, which can provide an additional source of power/recharging.

The batteries 130 can provide power to a fan 136, which can be installed within the protective suit 14A. The fan 136 can provide cooling for the user 2 wearing the protective suit 14A. Air brought into the protective suit 14A by the fan 136 can enter an ultraviolet air disinfection component incorporated into the suit for sterilization. For example, the ultraviolet air disinfection component can comprise a set of ultraviolet sources, which are capable of delivering a sufficient dose of ultraviolet radiation to a volume of air passing through the chamber to ensure that the air is sterilized. It is understood that the protective suit 14A can, in addition, be configured to enable attachment of a compressed air supply over the fan 136, e.g., when contamination of the environment 4 (FIG. 2) is too high to be effectively controlled by the ultraviolet radiation available in the protective suit 14A. The protective suit 14A can include an outflow duct to allow air to exit the protective suit. In this case, the outflow duct can be designed to not allow any air or other environmental particles to enter the protective suit 14A (e.g., include a filter unit, flaps, and/or the like). Furthermore, the outflow duct can include an ultraviolet air disinfection component as described herein, to ensure that no air inadvertently entering through the outflow duct and/or any of the components of the outflow duct is contaminated.

In an embodiment, the protective suit 14A can include a first fan 136 associated with an ultraviolet air disinfection component, and a set of internal fans, which circulate the sterilized air exiting the ultraviolet air disinfection component within the protective suit 14A. In this case, the first fan 136 can be a slow operating fan capable of driving a volume of air into the ultraviolet air disinfection component. The sterilized air can be driven by internal fan(s) into the protective suit 14A at a higher velocity to provide cooling. In an embodiment, the protective suit 14A can include a series of duct tubes exiting the ultraviolet air disinfection component and delivering air to different regions of the protective suit 14A. Additionally, an embodiment of the protective suit 14A can include a mechanism for cooling the air (e.g., water cooled, cooled using a thermoelectric cooler, and/or the like) to provide additional cooling of the user 2.

The protective suit 14A also can include a perspiration unit 138, which can assist in cooling the user 2. For example, the perspiration unit 138 can comprise a vessel containing a fluid (such as water) placed within the protective suit 14A. The vessel can be connected to an external surface of the suit by a set of tubes. The fluid can be allowed to travel from the vessel to the tube openings on the surface of the protective suit 14A and cool the external surface of the protective suit 14A through evaporation. The fluid can be driven by a pump incorporated on the protective suit 14A or travel through the tubes by a capillary action. Furthermore, an external fan, which can be included as part of the protective suit 14A, can be utilized to cool the external surface of the protective suit 14A.

As discussed herein, the protective suit 14A can include one or more devices capable of acquiring data corresponding to a physical condition of the user 2 wearing the protective suit 14A. For example, the protective suit 14A can include a thermometer to determine a temperature within the protective suit 14A, which can be used to adjust operation of the fan 136 and/or perspiration unit 138. An additional thermometer can be attached to the user 2 to determine if he/she has acquired a fever. Additionally, the protective suit 14A can include other types of internal sensors, such as gas and humidity sensors, humidity sensors attached to the skin of the user 2, a blood pressure sensor, a heart rate sensor, a heart rate variation monitor, an accelerometer (e.g., to measure tremors), a blood sugar sensor, a blood oxygen sensor, a skin perspiration sensor, and blood oxygen sensor, a pupil size variation monitor, brain wave (e.g., beta, alpha, theta, delta) sensors, event related potentials (ERP) sensors, and/or the like.

Additionally, the protective suit 14A can include a computer system, which can communicate data (e.g., using a wireless communications solution) regarding the user 2 and/or operation of the protective suit 14A to an external system, such as the monitoring and/or control system 11 and/or the supervisor 12 shown in FIG. 3. The computer system also can receive information, which can be provided to update the user 2 regarding a status of a sterilization procedure currently being performed on the protective suit 14A, an estimated amount of time remaining, fluorescence data regarding the surface of the protective suit 14A, and/or the like. Such information can be provided to the user 2 audibly and/or visually, e.g., via a region of a mask of the protective suit 14A or a mini screen mounted nearby. In the event sensory data indicates that the user 2 has acquired an infection, special procedures according to protocol can be employed to treat the user 2 and/or decontaminate the protective suit 14A and/or the disinfection chamber 40 described herein.

It is understood that all the parts of the human body are protected by the protective suit 14A. To this extent, the protective suit 14A is equipped with gloves forming sealed connection to the sleeves of the protective suit 14A. The user 2 can enter the protective suit 14A through a zipper opening in the middle of the protective suit 14A. The protective suit 14A can include a section that covers the zipper opening (e.g., using a hook and latch fastener or the like). For further protection, the zipper opening also can contain one or more ultraviolet sources for disinfecting an area around the zipper opening. To provide the user 2 with additional disinfection resources, the protective suit 14A can include a set of ultraviolet disinfection sources 64A, 64B located in the gloves, allowing the user 2 to use his/her hands as a disinfection wand. The user 2 can control an intensity and/or other characteristics of the ultraviolet disinfection sources 64A, 64B (e.g., shape of ultraviolet beam) using any type of interface, such as a set of buttons located on the sleeve(s) of the protective suit 14A, a set of buttons located elsewhere (for instance on the body of the protective suit 14A or in a remote control location), and/or the like. When the ultraviolet disinfection sources 64A, 64B are activated, the protective suit 14A also can provide a visible indicator, such as a visible light source to provide feedback to the user 2 that the ultraviolet disinfection sources 64A, 64B are on. In an embodiment, the ultraviolet disinfection sources 64A, 64B can be selectively operated as ultraviolet fluorescent sources, which can enable the user 2 to direct fluorescence-inducing ultraviolet radiation to various locations on the protective suit 14A.

Figure 14:
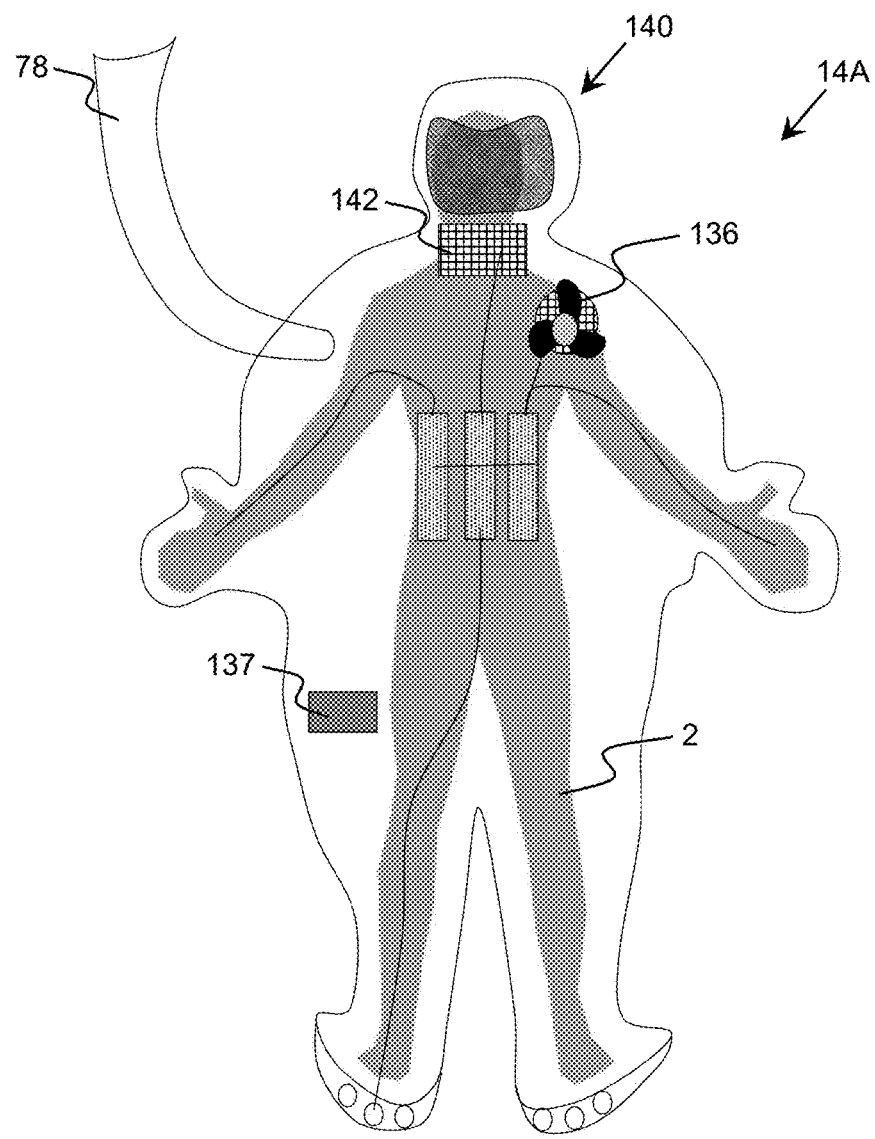

As discussed herein, the protective suit 14A can be sterilized within a decontamination chamber described herein. FIG. 14 shows an illustrative embodiment for facilitating effective sterilization of a protective suit 14B according to an embodiment. In this case, the protective suit 14B can include a fan 136 operable to create a positive pressure within the protective suit 14B, thereby causing the protective suit 14B to expand, reducing the presence of any folds in the material of the protective suit 14B. The protective suit 14B can include an air output duct 137, which can enable air to selectively escape the protective suit 14B during the sterilization process, e.g., after a target internal pressure is attained. In another embodiment, the protective suit 14B can be connected to an outside sleeve 78, which can be implemented as part of a decontamination chamber 40 (FIG. 4) and operated to deliver air to the interior of the protective suit 14B as part of a sterilization process described herein.

In an embodiment, determination of the presence and location of folds in the fabric of the protective suit 14B can be made using data acquired by an imaging component 58 (FIG. 4) of the decontamination chamber 40 and the pressure can be adjusted based on the feedback of the imaging component 58 up to a maximum pressure level. In an embodiment, the monitoring and/or control system 11 (FIG. 4) can operate the outside sleeve 78 to deliver pulsed pressure waves, which are used to inflate the protective suit 14B together with the treatment component 52, cleaning component 54, and/or fluorescent component 59 synchronized with the timing of the pulsed pressure waves. Furthermore, a protective suit 14B can contain regions comprising a fabric having a layered structure of at least two layers weakly connected, where the pressurized air can be delivered between two layers. As used herein, "weakly connected" means layers that are connected at some lateral points, but have sufficient space between the layers to allow air to go into the channel or domain located between the layers.

For complete disinfection after the user 2 has removed the protective suit 14B, the protective suit 14B can include a set of internally located ultraviolet sources, e.g., embedded into various locations of the material of the protective suit 14B, which can be turned on to irradiate the internal surface of the protective suit 14B. Alternatively, an ultraviolet source assembly can be inserted into the protective suit 14B for internally sterilizing the protective suit 14B. For instance, such a source assembly can have a shape similar to that of an individual, with protrusions containing ultraviolet sources configured to penetrate the sleeve portion, glove portion, leg portion, and head portion of the protective suit 14B, and a main portion of the assembly designed to irradiate the internal body portion of the protective suit 14B. Such an assembly can be fabricated using a flexible material for facilitating insertion into and removal from the protective suit 14B, which is also transparent to ultraviolet radiation. The assembly can be configured to stretch the material of the protective suit 14B to improve an overall exposure of the internal surface area of the protective suit 14B to ultraviolet radiation. Fabrication of such an assembly can be performed using any solution. For example, illustrative light guiding structures are shown and described in U.S. patent application Ser. Nos. 14/853,057 and 14/853,014, both of which were filed on 14 Sep. 2015 and both of which are hereby incorporated by reference. An illustrative assembly described in conjunction with illuminating an interior surface of footwear is described in U.S. patent application Ser. No. 14/853,036, which was filed on 14 Sep. 2015 and which is hereby incorporated by reference. Additionally, the protective suit 14B can again be inflated as described herein with the assembly inserted inside.

The protective suits 14A, 14B include a mask 140 completely enclosing the user's head. The mask 140 can be equipped with a respirator comprising an ultraviolet air disinfection unit 142, also powered by the batteries 130, which enables the user 2 to breathe disinfected air while wearing the protective suit 14A, 14B. To this extent, the ultraviolet air disinfection unit 142 can be configured to deliver sufficient ultraviolet radiation to the volume of air to sterilize the air prior to inhaling by the user 2. In an embodiment, the air disinfection unit 142 and the ultraviolet air disinfection component for the fan 136 and/or outflow duct described herein are configured in a similar manner.

Figure 15:
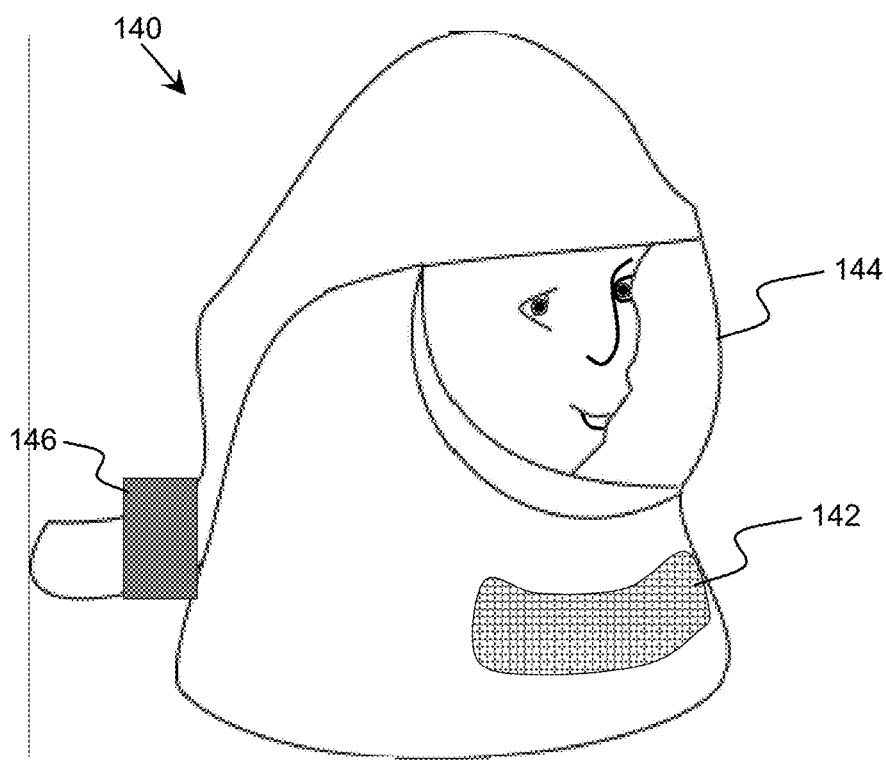

FIG. 15 shows an illustrative mask 140 according to an embodiment. The mask 140 includes an air disinfection unit 142, a glass portion 144, and an exhaust output 146, all of which are integrated into the material of the mask 140 in an air tight manner. During use, air from the ambient environment passes through the air disinfection unit 142 into an interior of the mask 140 and is breathed by the user 2. Exhaust air can be removed from the interior by the exhaust output 146, which can utilize a fan, or the like, to remove the air from the mask 140. In an embodiment, the exhaust output 146 includes an ultraviolet air disinfection component configured as described herein. The user 2 can view his/her environment through the glass portion 144.

Figure 16A:
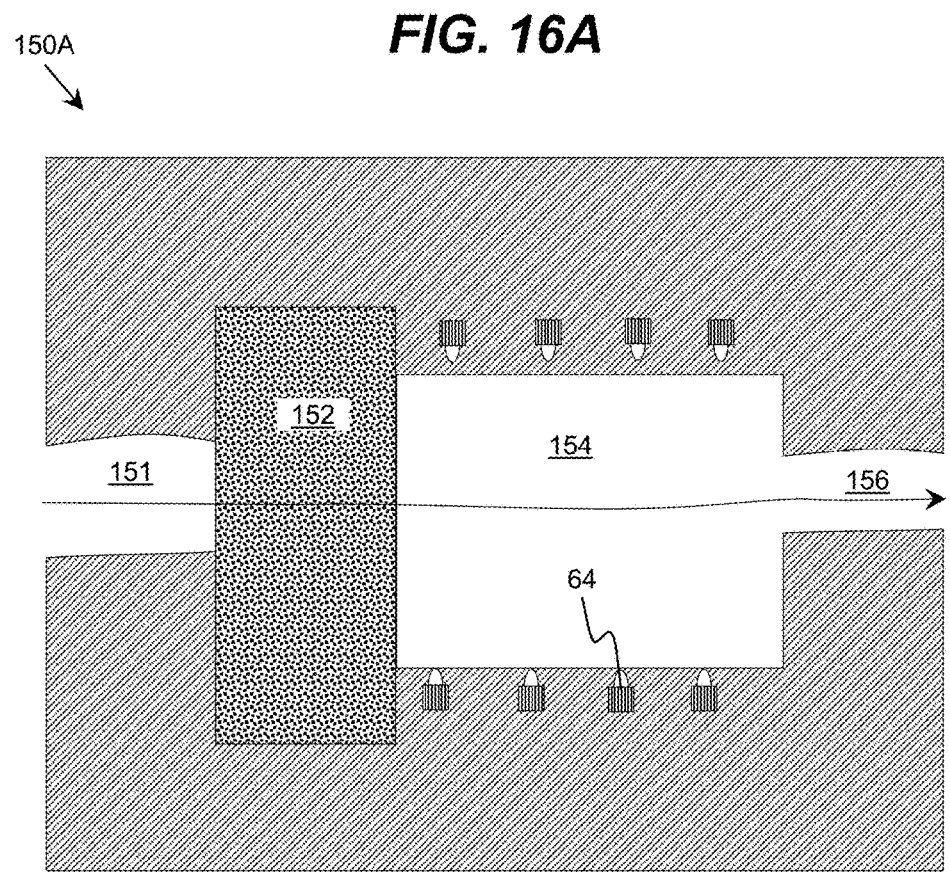
Figure 16C:
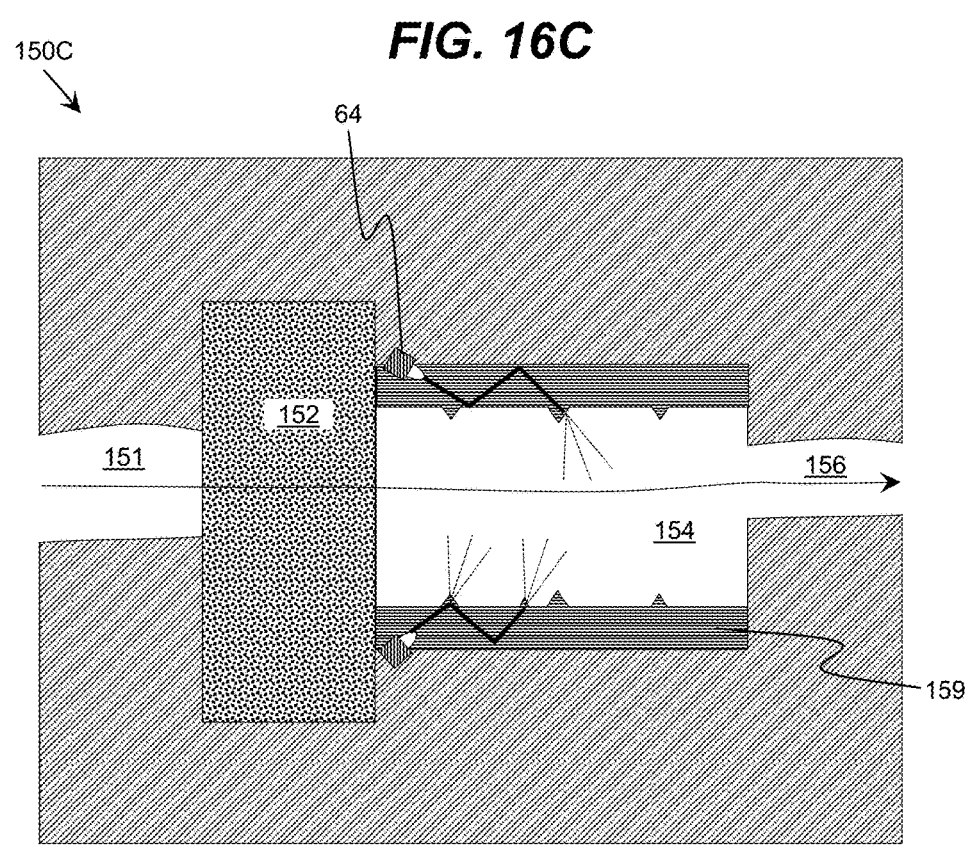

As discussed herein, an ultraviolet disinfection component can be utilized in conjunction with the fan 136, the air disinfection unit 142, the exhaust output 146, an outflow duct, and/or the like. FIGS. 16A-16C show illustrative ultraviolet disinfection components 150A-150C according to embodiments, each of which can be implemented in conjunction with the fan 136, the air disinfection unit 142, the exhaust output 146, an outflow duct, and/or the like. In each ultraviolet disinfection component 150A-150C, air from the ambient enters an inlet 151 and passes through a filtering unit 152. In an embodiment, the filtering unit 152 comprises a typical air filtering unit, such as a high efficiency particulate air (HEPA) filter, for removing particulates from the air. Furthermore, the filtering unit 152 can include an activated carbon-based filter, e.g., for filtration of volatile organic compounds, chemical vapors, smoke, and/or the like.

After exiting the filtering unit 152, the air enters an ultraviolet chamber 154, within which sufficient ultraviolet radiation to sterilize the air as it moves through the chamber 154 is emitted by a set of ultraviolet disinfection sources 64. Subsequently, the sterilized air exits the chamber 154 through a set of outflow passages 156. For example, when used in conjunction with the fan 136, multiple outflow passages 156 can direct the sterilized air to different regions within the protective suit. It is understood that various alternative arrangements can be utilized. For example, when used in conjunction with an outflow duct, the flow of the air can be reversed. In this case, air from the interior of the suit can first pass through the chamber 154 before exiting the suit through the filtering unit 152. In this arrangement, ambient air inadvertently entering the suit through the outflow duct will first be filtered by the filtering unit 152 and subsequently be sterilized within the chamber 154.

In an embodiment, the chamber 154 can comprise a reflective enclosure. In this case, at least the inner surface of the chamber 154 can comprise a reflective material described herein. In another embodiment, the set of ultraviolet disinfection sources 64 can be embedded in an ultraviolet transparent material described herein. In this case, at least some of the walls or portions of the walls (e.g., windows) of the chamber 154 can remain transparent to the ultraviolet radiation. Furthermore, the walls of the chamber 154 can include portions covered with reflective material, portions configured to promote total internal reflection of the ultraviolet radiation within the chamber 154, and/or the like. Regardless, it is understood that the ultraviolet disinfection sources 64 also can be located within the chamber 154 or remote from the chamber 154, in which case light guiding structures can be utilized to direct the ultraviolet radiation to various locations within the chamber 154.

It is understood that numerous variations of configurations of ultraviolet disinfection sources 64 and the chamber 154 are possible in embodiments. To this extent, the number and arrangement of ultraviolet disinfection sources 64 is only illustrative. Additional features can be included in the ultraviolet disinfection component, such as inclusion of a photo-catalyst, turbulence-inducing structures, reflective structures, and/or the like, within the chamber 154. Additionally, ultraviolet disinfection sources 64 can be configured to sterilize the filtering unit 152, the inlet 151, and/or the like.

In an embodiment, the chamber 154 includes one or more structures configured to promote mixing of the air and/or the ultraviolet radiation to provide an increased dose of ultraviolet radiation to the air within the chamber 154. For example, FIG. 16B shows an illustrative serpentine structure 158 located within the chamber 154. The serpentine structure 158 can force the air to flow in a serpentine pattern through the chamber 154, which can enable the air to receive an increased dose of ultraviolet radiation within the same chamber volume. For example, the serpentine structure can allow for improved diffusion of ultraviolet light throughout the chamber 154 and/or can provide additional air circulation around the chamber 154, prolonging the residence time of the air, thereby enabling the air to receive a required dose for sterilization. In an embodiment, the serpentine structure 158 is fabricated of an ultraviolet transparent material described herein (e.g., a fluoropolymer). As illustrated, the serpentine structure 158 can include one or more additional ultraviolet disinfection sources 64 embedded therein.

An embodiment of the ultraviolet disinfection component can further utilize diffuse ultraviolet radiation to provide a more uniform flux of ultraviolet radiation within the chamber 154. To this extent, in FIG. 16C, the ultraviolet disinfection component 150C is shown including light guiding structures 159 on the walls, which can be configured as shown and described in conjunction with FIG. 6B to emit diffusive ultraviolet light into the chamber 154. Embodiments of the ultraviolet chamber can be configured as shown and described in U.S. patent application Ser. No. 14/285,869, filed on 23 May 2014, and U.S. patent application Ser. No. 14/814,537, filed on 31 Jul. 2015, both of which are hereby incorporated by reference. Embodiments of the ultraviolet chamber also can include light guiding structures, such as are shown and described in U.S. patent application Ser. Nos. 14/853,057 and 14/853,014, both of which were filed on 14 Sep. 2015 and both of which are hereby incorporated by reference.

Other Embodiments

While shown and described herein as a method and system for sterilizing a surface, such as a surface of a protective suit, with ultraviolet light, it is understood that aspects of the invention further provide various alternative embodiments. For example, in one embodiment, the invention provides a computer program fixed in at least one computer-readable medium, which when executed, enables a computer system to treat a surface with ultraviolet light. To this extent, the computer-readable medium includes program code, such as the protection program 30 (FIG. 3), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the protection program 30 (FIG. 3), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for sterilizing a surface with ultraviolet light. In this case, the generating can include configuring a computer system, such as the computer system 20 (FIG. 3), to implement a method of treating a surface with ultraviolet light described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
    a disinfection chamber comprising:
        a plurality of ultraviolet disinfection sources configured to irradiate an object located within the disinfection chamber from a plurality of directions, wherein at least some of the plurality of ultraviolet disinfection sources emits UV-C electromagnetic radiation;
        a plurality of visible light sources co-located with the plurality of ultraviolet disinfection sources; and
        a set of cameras configured to acquire image data of the object from a plurality of directions; and
    a computer system including a set of computing devices, wherein the computer system is configured to perform a sterilization procedure for the object, wherein the sterilization procedure includes processing the image data to evaluate shadow data to adjust sterilization of the object using the plurality of ultraviolet disinfection sources.

2. The system of claim 1, wherein the decontamination chamber further includes a set of shower heads configured to direct a fluid toward the object.

3. The system of claim 1, the disinfection chamber further comprising a set of ultraviolet fluorescent sources configured to irradiate at least a portion of the object with ultraviolet radiation configured to induce fluorescence in a target contaminant, wherein the sterilization procedure further includes processing the image data to evaluate fluorescence data to adjust the sterilization of the object.

4. The system of claim 1, wherein the object comprises a protective suit worn by a user.

5. The system of claim 4, wherein the protective suit includes an ultraviolet air disinfection component for sterilizing ambient air prior to entering an interior of the protective suit.

6. The system of claim 5, wherein the protective suit includes a fan for directing air through the ultraviolet air disinfection component and into the protective suit.

7. The system of claim 4, further comprising means for providing instructions to the user.

8. The system of claim 7, wherein the instructions includes at least one of: audible instructions or visible instructions, of a change in position required of the user.

9. The system of claim 1, further comprising means for moving at least one of the plurality of ultraviolet disinfection sources.

10. The system of claim 9, wherein the means for moving selectively moves a focused beam of ultraviolet radiation emitted by each of the at least one of the plurality of ultraviolet disinfection sources along a surface of the object.

11. The system of claim 10, further comprising means for identifying a target area of the surface of the object, wherein the means for moving moves the focused beam to illuminate the target area of the surface.

12. The system of claim 1, further comprising a handheld ultraviolet unit configured to direct ultraviolet radiation onto an adjacent surface of the object.

13. The system of claim 12, wherein the handheld ultraviolet unit includes a second set of ultraviolet disinfection sources configured to irradiate the adjacent surface with a dose of ultraviolet radiation sufficient to sterilize the adjacent surface within five seconds.

14. A system comprising:
    a protective suit worn by a user, wherein the protective suit completely isolates the user from exposure to contaminants in an environment; and
    a disinfection chamber for sterilizing an exterior surface of the protective suit, the disinfection chamber comprising:
        a set of ultraviolet disinfection sources configured to irradiate the protective suit from a plurality of directions with UV-C electromagnetic radiation;
        a set of visible light sources co-located with the set of ultraviolet disinfection sources;
        a set of ultraviolet fluorescent sources configured to irradiate at least a portion of the protective suit with ultraviolet radiation configured to induce fluorescence in a target contaminant; and
        a set of cameras configured to acquire image data of the protective suit from a plurality of directions; and
    a computer system including a set of computing devices, wherein the computer system is configured to perform a sterilization procedure for the protective suit, wherein the sterilization procedure includes processing the image data to evaluate at least one of: shadow data or fluorescence data, to adjust sterilization of the protective suit using the set of ultraviolet disinfection sources.

15. The system of claim 14, further comprising means for providing the user instructions during the sterilization procedure.

16. The system of claim 14, wherein the protective suit includes:
- a set of sensors for acquiring data regarding the user; and
- means for providing the data for evaluation by a supervisor.

17. The system of claim 14, wherein the protective suit includes an ultraviolet air disinfection component for sterilizing ambient air prior to entering an interior of the protective suit, wherein the ultraviolet air disinfection component includes:
- a filtering unit for filtering particulates from the environment;
- an ultraviolet chamber for holding air filtered by the filtering unit; and
- a set of ultraviolet decontamination sources configured to expose the filtered air to a dose of ultraviolet radiation sufficient to sterilize the filtered air.

18. A system including:
- a handheld ultraviolet unit configured to induce fluorescence in a target contaminant on an adjacent surface, detect the fluorescence on the adjacent surface, and provide location data regarding a location of the fluorescence for processing by an external computer system;
- a disinfection chamber comprising:
  - a set of ultraviolet disinfection sources configured to irradiate an object located within the disinfection chamber from a plurality of directions with UV-C electromagnetic radiation;
  - a set of visible light sources co-located with the set of ultraviolet disinfection sources; and
  - a set of cameras configured to acquire image data of the object from a plurality of directions; and
- a computer system including a set of computing devices, wherein the computer system is configured to perform a sterilization procedure for the object, wherein the sterilization procedure includes adjusting operation of the set of ultraviolet disinfection sources based on the location data and the image data.

19. The system of claim 18, wherein the disinfection chamber further includes a set of shower heads configured to direct a fluid toward the object, wherein the sterilization procedure further includes adjusting operation of the set of shower heads based on the location data and the image data.

20. The system of claim 18, wherein the disinfection chamber further includes means for reducing shadows on the object, wherein the sterilization procedure includes processing the image data to evaluate a presence of shadows on the object and adjusting operation of the means for reducing based on the presence of shadows.

* * * * *